(12) United States Patent
Yamano

(10) Patent No.: US 8,776,604 B2
(45) Date of Patent: Jul. 15, 2014

(54) ULTRASONIC PROBE, ULTRASONIC TESTING EQUIPMENT, AND ULTRASONIC TESTING METHOD

(75) Inventor: Masaki Yamano, Suita (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 0 days.

(21) Appl. No.: 13/312,213

(22) Filed: Dec. 6, 2011

(65) Prior Publication Data

US 2012/0167690 A1 Jul. 5, 2012

Related U.S. Application Data

(62) Division of application No. 11/990,936, filed as application No. PCT/JP2006/316869 on Aug. 28, 2006, now Pat. No. 8,490,490.

(30) Foreign Application Priority Data

Aug. 26, 2005 (JP) .................................. 2005-245475
Aug. 18, 2006 (JP) .................................. 2006-223541

(51) Int. Cl.
*G01N 29/24* (2006.01)
*G01N 29/26* (2006.01)

(52) U.S. Cl.
USPC .............................................. 73/602; 73/622

(58) Field of Classification Search
USPC ............ 73/622, 623, 632, 633, 634, 640, 641
See application file for complete search history.

(56) References Cited

U.S. PATENT DOCUMENTS

| 4,817,016 | A | * | 3/1989 | Thompson et al. | ............. | 702/39 |
| 5,421,200 | A | * | 6/1995 | Casarcia et al. | ................ | 73/632 |
| 5,447,070 | A | * | 9/1995 | Patzke et al. | .................... | 73/621 |
| 5,485,751 | A | * | 1/1996 | Karbach et al. | ................ | 73/618 |
| 5,974,889 | A | * | 11/1999 | Trantow | ......................... | 73/624 |
| 2011/0088476 | A1 | * | 4/2011 | Yamano et al. | ................ | 73/632 |

FOREIGN PATENT DOCUMENTS

| JP | 48-24785 | 3/1973 |
| JP | 55-116251 | 9/1980 |
| JP | 59-163563 | 9/1984 |
| JP | 61-223553 | 10/1986 |
| JP | 64-43906 | 2/1989 |
| JP | 4-142456 | 5/1992 |
| JP | 5-84464 | 4/1993 |
| JP | 2005-211973 | 8/2005 |

* cited by examiner

*Primary Examiner* — Peter Macchiarolo
*Assistant Examiner* — Rose M Miller
(74) *Attorney, Agent, or Firm* — Clark & Brody

(57) ABSTRACT

An ultrasonic probe for detecting a flaw by ultrasonic waves in a tubular test object includes a plurality of transducers arranged along an annular curved surface, wherein the annular curved surface is obtained by cutting a predetermined spheroid with two parallel planes facing to each other that do not pass through a center of the spheroid and do not sandwich the center of the spheroid, said two parallel planes being orthogonal to a rotational axis of the spheroid. A shape of said annular curved surface is determined so that when transducers appropriately selected from said plurality of transducers are caused to transmit and receive ultrasonic waves, respective internal refraction angles $\theta\kappa$ of the ultrasonic waves are approximately equivalent regardless of propagation directions of the ultrasonic waves.

10 Claims, 16 Drawing Sheets

ULTRASONIC PROBE, ULTRASONIC TESTING EQUIPMENT, AND ULTRASONIC TESTING METHOD

TECHNICAL FIELD

The present invention relates to an ultrasonic probe, an ultrasonic testing equipment and an ultrasonic testing method for detecting a flaw existing on a tubular test object such as a steel pipe or tube using an ultrasonic wave, and a manufacturing method of a seamless pipe or tube using the method, and in particular, to an ultrasonic probe, an ultrasonic testing equipment and an ultrasonic testing method capable of quickly detecting flaws having various tilt angles with respect to an axial direction of a tubular test object with high precision, and a manufacturing method of a seamless pipe or tube using the method.

BACKGROUND ART

As demand for higher quality pipes or tubes grows in recent years, there is an increasing trend that nondestructive test standards for the pipes or tubes (hereinafter referred to as "pipes" when deemed appropriate) are becoming more stringent.

For example, a seamless pipe, which is a typical pipe, is manufactured by punching a billet with a piercer to form a hollow shell and rolling the hollow shell with a mandrel mill or the like. The seamless pipe has flaws having various tilt angles (hereinafter referred to as "tilted flaws" when deemed appropriate) with respect to the axial direction.

A tilted flaw is believed to be caused by deformation in the axial direction of a longitudinal crack originally existing on the billet in the above manufacturing process or transfer of a flaw existing on a guide face of a guide shoe for maintaining a path center of a hollow shell. Therefore, the tilt angle of the tilted flaw with respect to the axial direction of the seamless pipe changes depending on a difference in a pipe diameter of the seamless pipe or a cause for occurrence thereof. That is, there are tilted flaws with various tilt angles on the seamless pipe.

Since there is a trend of tighter service conditions of the seamless pipes from year to year, higher quality is demanded and accurate detection of the above tilted flaws is also sternly demanded.

Conventionally, various methods for detecting the tilted flaws existing on the seamless pipes have been proposed.

In Japanese Laid-Open Patent Publication No. 55-116251 (hereinafter referred to as "Patent Literature 1"), for example, a method for detecting a tilted flaw by arranging an ultrasonic probe at an appropriate position and tilt angle depending on the position and tilt angle of the tilted flaw to be detected is proposed.

However, the method described in Patent Literature 1 has a problem that extremely much time and manpower are needed because the tilt angle of the ultrasonic probe must be changed each time in accordance with the tilt angle of the tilted flaw to be detected. Also, to detect tilted flaws with various tilt angles existing on the seamless pipe in one round of flaw-detecting work, as described above, many ultrasonic probes must be provided, each of which is arranged with a different tilt angle. That is, there are problems that large equipment is required and soaring costs are entailed, in addition to complicated arrangements/settings and calibration of ultrasonic probes.

To solve the problems of the method described in the above Patent Literature 1, a flaw detecting method that applies an ultrasonic phased array probe in which a plurality of transducers (elements for transmitting/receiving ultrasonic waves) are arranged in a single row is proposed in Japanese Laid-Open Patent Publication No. 61-223553 (hereinafter referred to as "Patent Literature 2"). More specifically, ultrasonic shear waves are propagated within the pipe by aligning an arrangement direction of the transducers with the axial direction of the pipe and arranging the ultrasonic probe decentralized from an axial center of the pipe. Then, according to this method, the tilted flaws with the various tilt angles are detected by changing the tilt angle (tilt angle with respect to the axial direction of the pipe) of ultrasonic waves transmitted and received by the ultrasonic probe using electronic scanning that electrically controls transmission/reception time-shift of the ultrasonic wave by each transducer.

However, two main problems (first problem and second problem) shown below exist in the method described in Patent Literature 2.

<First Problem>

FIG. 1 shows a diagram illustrating an example of a relation between the tilt angle (angle formed by an extension direction of the tilted flaw and the axial direction of the pipe) of the tilted flaws and echo intensity according to an ultrasonic testing method applying an ultrasonic phased array probe, verified by an experiment conducted by the inventors of the present invention. More concretely, FIG. 1 shows echo intensity (relative intensity when the echo intensity of a tilted flaw with the tilt angle 0° is defined to be 0 dB) of each tilted flaw when, in a state where an ultrasonic phased array probe equivalent to that described in Patent Literature 2 is arranged with a constant eccentricity from the axial center of the pipe, the tilt angle of the ultrasonic wave is changed by electronic scanning in accordance with the tilt angle of each tilted flaw so that the extension direction of the tilted flaw and a propagation direction (propagation direction viewed from a normal direction of a tangential plane of the pipe including an incident point of the ultrasonic wave) of the ultrasonic wave transmitted by the ultrasonic probe are orthogonal to each other. The inventors of the present invention have found a problem that, as shown in FIG. 1, echo intensity is different depending on the tilt angle of the tilted flaw even if the tilted flaw is of the same size (0.5 mm in depth and 25 mm in length).

As described above, the inventors of the present invention have found that the method described in Patent Literature 2 has the problem that the echo intensity is different depending on the tilt angle of the tilted flaw and there is a possibility that this problem may prevent detection of a harmful flaw or lead to over-detection of minute flaws that need not be detected.

<Second Problem>

If electronic scanning for electrically controlling transmission/reception time-shift of the ultrasonic wave by each transducer of an ultrasonic phased array probe described in Patent Literature 2 is used to change the tilt angle of the ultrasonic wave transmitted and received by the ultrasonic probe, electronic scanning must be repeated as many times as required depending on the tilt angle of the tilted flaw to be detected in a specific area of the pipe. That is, for example, to detect three tilted flaws with different tilt angles, electronic scanning must be repeated three times in the specific area of the pipe, and ultrasonic testing efficiency is reduced to ⅓ when compared with detection of flaws with a unidirectional tilt angle.

More concretely, one round of ultrasonic testing in the specific area of the pipe, though dependent on, in addition to an outer diameter and thickness of the pipe, distance between the ultrasonic probe and the pipe and the like, takes approximately 50 to 100 μsec. That is, the maximum number of times of ultrasonic testing per unit time (ultrasonic testing speed) in the specific area of the pipe is 10,000 to 20,000 times per second. Therefore, a change speed (change frequency) of the tilt angle of the ultrasonic wave by the electronic scanning is also compelled to be about 10,000 to 20,000 times per second or less, and even if the electronic scanning itself is much faster than mechanical scanning, ultrasonic testing efficiency will decrease as the number of tilt angles of the tilted flaws to be detected increases.

As described above, the method described in Patent Literature 2 has the problem that the ultrasonic testing efficiency goes down as the number of the tilt angles of the tilted flaws to be detected increases.

In Japanese Laid-Open Patent Publication No. 59-163563 (hereinafter referred to as "Patent Literature 3"), on the other hand, a method for causing the ultrasonic wave to enter in any direction using a group of transducers arranged in a matrix state in order to detect the tilted flaws with the various tilt angles is proposed. More concretely, an incident direction of the ultrasonic wave is arbitrarily changed by selecting an appropriate number of arbitrary transducers from the group of transducers and by performing electronic scanning for electrically controlling transmission/reception time-shift (driving time) thereof. Then, it is disclosed that patterns to change the incident directions of the ultrasonic wave are stored in advance as a program.

However, the first problem that echo intensity changes in accordance with the tilt angle of each tilted flaw, as described above, is not mentioned and further, in order to solve the problem, nothing is disclosed about which change pattern should be used to change the incident directions of the ultrasonic wave in Patent Literature 3. In addition, there is a problem similar to the second problem of the method described in Patent Literature 2. That is, there is the problem that the ultrasonic testing efficiency decreases because electronic scanning must be repeated as many times as the number of tilt angles of the tilted flaws to be detected.

DISCLOSURE OF THE INVENTION

Problems of the above-described conventional technologies are not limited to a case where a test object is a seamless pipe, but are common to ultrasonic testing of all types of tubular test objects in which tilted flaws may occur including a welded pipe such as a spiral pipe, and a hollow axle.

The present invention has been developed to solve such problems of conventional technologies, and it is an object of the present invention to provide an ultrasonic probe, an ultrasonic testing equipment and an ultrasonic testing method capable of quickly detecting flaws having various tilt angles with respect to an axial direction of a tubular test object with high precision, and a manufacturing method of a seamless pipe using the probe, apparatus and method.

To solve the above-described problems, the inventors of the present invention studied what is described below earnestly.

FIG. 2 shows diagrams illustrating relations between a tilt angle of a tilted flaw and an angle of incidence of an ultrasonic wave with the tilted flaw in a ultrasonic testing method applying an ultrasonic phased array probe, as found by the inventors of the present invention based on numerical calculation. More concretely, FIG. 2 shows the angle of incidence of the ultrasonic wave with each tilted flaw in a case where an eccentricity when the ultrasonic phased array probe equivalent to that described in Patent Literature 2 is arranged by decentralizing from an axial center of a pipe (ratio of thickness to outer diameter=11%) is appropriately set (circumferential angle of incidence $\alpha i$ with the pipe determined in accordance with the eccentricity is set to 10°, 16°, and 19°), and the tilt angle of the ultrasonic wave is changed by electronic scanning in accordance with the tilt angle of each tilted flaw so that an extension direction of the tilted flaw and a propagation direction of the ultrasonic wave transmitted by the ultrasonic probe are orthogonal to each other. FIG. 2 (a) shows an angle of incidence (internal refraction angle) $\theta k$ with an internal surface flaw existing on an internal surface of a pipe, and FIG. 2 (b) shows an angle of incidence (external refraction angle) $\theta r$ with an external surface flaw existing on an external surface of the pipe. As shown in FIG. 2, the inventors of the present invention have found that, for both internal and external surface flaws, the tilt angle of the ultrasonic wave changes in accordance with the tilt angle of the tilted flaw. The inventors of the present invention have also found that echo intensity is different depending on the tilt angle of each tilted flaw, as described above (See FIG. 1), because even if the tilt angle of the ultrasonic wave is changed by electronic scanning in accordance with the tilt angle of each tilted flaw so that the extension direction of the tilted flaw and the propagation direction of the ultrasonic wave transmitted by the ultrasonic probe are orthogonal to each other, as shown in FIG. 2, the external refraction angle and internal refraction angle change in accordance with the tilt angle of each tilted flaw (in accordance with the propagation direction of the ultrasonic wave).

With the above findings, the inventors of the present invention have thought out that (1) by setting a ultrasonic testing condition so that external refraction angle (or internal refraction angle) become approximately equivalent regardless of the propagation direction of the ultrasonic wave, it becomes possible to obtain approximately equivalent echo intensity of external surface flaws (or internal surface flaws) regardless of the propagation direction of the ultrasonic wave and to detect flaws with various tilt angles with high precision, and (2) by adopting a configuration in which ultrasonic waves can approximately simultaneously be transmitted to and received from a tubular test object in a plurality of different propagation directions, the problem of reduced ultrasonic testing efficiency can be solved, and as a result, the flaws with the various tilt angles can quickly be detected with high precision.

The present invention has been accomplished with the above-described findings of the inventors. That is, the present invention provides an ultrasonic testing method including the steps of arranging an ultrasonic probe having a plurality of transducers so as to face a tubular test object, and causing transducers appropriately selected from the plurality of transducers to transmit and receive ultrasonic waves so that the ultrasonic waves are propagated in the tubular test object in a plurality of different propagation directions, wherein a ultrasonic testing condition by the ultrasonic probe is set so that respective external refraction angles $\theta r$ of the ultrasonic wave in the plurality of propagation directions are approximately equivalent and/or respective internal refraction angles $\theta k$ of the ultrasonic wave in the plurality of propagation directions are approximately equivalent.

According to the invention, if the ultrasonic testing condition by the ultrasonic probe is set so that respective external refraction angles $\theta r$ of the ultrasonic wave in the plurality of propagation directions are approximately equivalent, approximately equivalent echo intensity of the external surface flaw can be obtained regardless of the plurality of propagation directions. Also, if the ultrasonic testing condition by the ultrasonic probe is set so that the respective internal refraction angles $\theta k$ of the ultrasonic wave in the plurality of propagation directions are approximately equivalent, approximately equivalent echo intensity of the internal surface flaw can be obtained regardless of the plurality of propagation directions. Furthermore, if the ultrasonic testing condition by the ultrasonic probe is set so that both the respective external refraction angles θr and the respective internal refraction angles θk of the ultrasonic wave in the plurality of propagation directions are approximately equivalent, approximately equivalent echo intensity of the external surface flaw and the internal surface flaw can be obtained regardless of the plurality of propagation directions. Therefore, the plurality of flaws (external surface flaws and/or internal surface flaws) respectively extending in directions orthogonal to the plurality of propagation directions can be detected with high precision.

Also, by approximately simultaneously transmitting the ultrasonic wave to and receiving the same from the tubular test object in the plurality of different propagation directions, the plurality of flaws respectively extending in the directions orthogonal to the propagation directions can be quickly detected.

According to the ultrasonic testing equipment method in the present invention, as described above, the flaws with various tilt angles with respect to the axial direction of the tubular test object can be quickly detected with high precision. The "propagation direction of the ultrasonic wave" in the present invention means the propagation direction of the ultrasonic wave viewed from the normal direction of a tangential plane of the tubular test object including an incident point of the ultrasonic wave. The "external refraction angle" means the angle θr formed, on a propagation plane of the ultrasonic wave of the tubular test object P, by a normal L1 of the tubular test object P and the ultrasonic wave U (central line of an ultrasonic wave beam) at a point B on the external surface of the tubular test object P reached by the ultrasonic wave U (central line of the ultrasonic wave beam) after entering the tubular test object P (See FIG. 4 (d)). The "internal refraction angle" means the angle θk formed, on the propagation plane of the ultrasonic wave of the tubular test object P, by a normal L2 of the tubular test object P and the ultrasonic wave U (central line of the ultrasonic wave beam) at a point A on the internal surface of the tubular test object P reached by the ultrasonic wave U (central line of the ultrasonic wave beam) after entering the tubular test object P (See FIG. 4 (d)). Furthermore, "respective external (or internal) refraction angles of the ultrasonic wave in the plurality of propagation directions are approximately equivalent" means that external (or internal) refraction angles have a range of variation of up to 10°.

As a concrete method of making the respective external refraction angles θr of the ultrasonic wave in the plurality of propagation directions approximately equivalent and/or the respective internal refraction angles θk of the ultrasonic wave in the plurality of propagation directions approximately equivalent, as described above, for example, a method of using the ultrasonic probe in which a plurality of transducers are arranged in a matrix state can be considered. That is, preferably a method is adopted wherein the ultrasonic probe has the plurality of transducers arranged in a matrix state on a plane or curved surface, and the transducers are selected so that the respective external refraction angles θr of the ultrasonic wave in the plurality of propagation directions are approximately equivalent and/or the respective internal refraction angles θk of the ultrasonic wave in the plurality of propagation directions are approximately equivalent. Incidentally, "the plurality of transducers arranged on the curved surface" in the present invention is used to include, in addition to a case where the transducers (transducer surfaces of the respective transducers) are formed on the curved surface so that part of the curved surface and a shape of the transducers match, a case where the respective transducers (transducer surfaces of the respective transducers) are formed in a plane shape and are respectively arranged to contact the curved surface.

Transducers to be selected so that the respective external refraction angles θr of the ultrasonic wave in the plurality of propagation directions are approximately equivalent can more specifically be determined, for example, as shown below. That is, a circumferential angle of incidence αi and an axial angle of incidence βi of the ultrasonic wave into the tubular test object in the plurality of propagation directions are respectively determined based on the following equation (1) so that the respective external refraction angles θr of the ultrasonic wave represented by the following equation (1) in the plurality of propagation directions are approximately equivalent, and the transducers are selected so that the determined circumferential angle of incidence αi and axial angle of incidence βi are obtained:

$$\theta r = \sin^{-1}(\{(Vs/Vi)^2 \cdot (\sin^2\beta i + \cos^2\beta i \cdot \sin^2\alpha i)\}^{1/2}) \quad (1)$$

where, in the above equation (1), Vs means a propagation velocity of the ultrasonic wave propagated in the tubular test object, and Vi means the propagation velocity of the ultrasonic wave in a coupling medium filled between the ultrasonic probe and the tubular test object. Also, the "circumferential angle of incidence" in the present invention means the angle αi formed, on a circumferential cross section of the tubular test object P, by a normal L3 of the tubular test object P and the ultrasonic wave U (central line of the ultrasonic wave beam) at an incident point O of the ultrasonic wave U (central line of the ultrasonic wave beam) (See FIG. (b)). Furthermore, the "axial angle of incidence" in the present invention means the angle βi formed, on an axial cross section of the tubular test object P, by a normal L4 of the tubular test object P and the ultrasonic wave U (central line of the ultrasonic wave beam) at an incident point O of the ultrasonic wave U (central line of the ultrasonic wave beam) (See FIG. (c)).

Transducers to be selected so that the respective internal refraction angles θk of the ultrasonic wave in the plurality of propagation directions are approximately equivalent can more specifically be determined, for example, as shown below. That is, the circumferential angle of incidence αi and the axial angle of incidence βi of the ultrasonic wave into the tubular test object in the plurality of propagation directions are respectively determined based on the following equations (1) to (6) so that the respective internal refraction angles θk of the ultrasonic wave represented by the following equation (2) in the plurality of propagation directions are approximately equivalent, and the transducers are selected so that the determined circumferential angle of incidence αi and axial angle of incidence βi are obtained:

$$\theta k = \cos^{-1}(\cos\theta r \cdot \cos\phi - \sin\theta r \cdot \cos\gamma \cdot \sin\phi) \quad (2)$$

where the external refraction angle θr, a propagation angle γ, and an angle φ in the above equation (2) are represented respectively by the following equations (1), (3), and (4):

$$\theta r = \sin^{-1}(\{(Vs/Vi)^2 \cdot (\sin^2\beta i + \cos^2\beta i \cdot \sin^2\alpha i)\}^{1/2}) \quad (1)$$

$$\gamma = \tan^{-1}\left(\frac{\sin\beta i}{\cos\beta i \cdot \sin\alpha i}\right) \quad (3)$$

-continued $$\phi = \sin^{-1}(k \cdot \sin\theta') - \theta' \quad (4)$$

where, in the above equation (1), Vs means the propagation velocity of the ultrasonic wave propagated in the tubular test object, and Vi means the propagation velocity of the ultrasonic wave in the coupling medium filled between the ultrasonic probe and the tubular test object; and k and θ' in the above equation (4) are represented respectively by the following equations (5) and (6):

$$k = \frac{1}{1 - 2(t/D)} \quad (5)$$

$$\theta' = \cos\gamma \cdot \tan\theta r \quad (6)$$

where t/D in the above equation (5) means a ratio of thickness to outer diameter of the tubular test object. The "propagation angle" in the present invention means the angle γ formed by the propagation direction (propagation direction viewed from the normal direction of the tangential plane of the tubular test object P including the incident point O of the ultrasonic wave) of the ultrasonic wave (central line of the ultrasonic wave beam) having entered the tubular test object P and a circumferential tangent L of the tubular test object P passing through the incident point O (See FIG. (a)).

On the other hand, as the concrete method of making the respective external refraction angles θr of the ultrasonic wave in the plurality of propagation directions approximately equivalent and/or the respective internal refraction angles θk of the ultrasonic wave in the plurality of propagation directions approximately equivalent, as described above, for example, a method of using an ultrasonic probe having the plurality of transducers arranged along a predetermined annular curved surface can be considered. That is, preferably a method is adopted wherein the ultrasonic probe has the plurality of transducers arranged along an annular curved surface obtained by cutting a predetermined spheroid with two parallel planes facing to each other that do not pass through a center of the spheroid and do not sandwich the center of the spheroid, said two parallel planes being orthogonal to the rotational axis of the spheroid, in the step of arranging the ultrasonic probe so as to face the tubular test object, the ultrasonic probe is arranged so that a longer axis direction of the ultrasonic probe is along an axial direction of the tubular test object, a shorter axis direction of the ultrasonic probe is along a circumferential direction of the tubular test object, and the center of the spheroid correctly faces an axial center of the tubular test object, and a shape of the annular curved surface is determined so that the respective external refraction angles θr of the ultrasonic wave in the plurality of propagation directions are approximately equivalent, and/or the respective internal refraction angles θk of the ultrasonic wave in the plurality of propagation directions are approximately equivalent. The "plurality of transducers arranged along the annular curved surface" in the present invention is used to include, in addition to a case where the respective transducers (transducer surfaces of the respective transducers) are formed on the curved surface so that part of the annular curved surface and the shape of the transducers match, a case where the respective transducers (transducer surfaces of the respective transducers) are formed in a plane shape and are respectively arranged to contact the annular curved surface. Also, the "the center of the spheroid correctly faces an axial center of the tubular test object" in the present invention means that the straight line, which passes through the center of the spheroid and is orthogonal to said two parallel planes (i.e. corresponding to the rotational axis of the spheroid), passes through an axial center of the tubular test object. Also, the "spheroid" in the present invention is used as a term including a sphere whose longer axis and shorter axis are equal.

The shape of the annular curved surface so that the respective external refraction angles θr of the ultrasonic wave in the plurality of propagation directions are approximately equivalent can be determined. That is, respective angles of incidence θw of the ultrasonic wave into the tubular test object in the plurality of propagation directions are calculated based on the following equation (7) so that the respective external refraction angles θr of the ultrasonic wave represented by the following equation (7) in the plurality of propagation directions are approximately equivalent, and the shape of the annular curved surface is determined so that the calculated angle of incidence θw is obtained:

$$\sin\theta r = Vs/Vi \cdot \sin\theta w \quad (7)$$

where, in the above equation (7), Vs means the propagation velocity of the ultrasonic wave propagated in the tubular test object, and Vi means the propagation velocity of the ultrasonic wave in the coupling medium filled between the ultrasonic probe and the tubular test object. The "angle of incidence of the ultrasonic wave into the tubular test object" in the present invention means the angle θw formed, on the propagation plane of the ultrasonic wave of the tubular test object P, by a normal L3 of the tubular test object P and the ultrasonic wave U (central line of the ultrasonic wave beam) at the incident point O of the ultrasonic wave U (central line of the ultrasonic wave beam) (See FIG. 6 (d)). If the angle of incidence θw is determined, the refraction angle θr is uniquely determined by Snell's law. Thus, "setting the angle of incidence θ" in the present invention is a concept that includes not only literally the setting of the angle of incidence θw, but also the setting of the refraction angle θr.

The shape of the annular curved surface so that the respective internal refraction angles θk of the ultrasonic wave in the plurality of propagation directions are approximately equivalent can be determined. That is, the respective angles of incidence θw of the ultrasonic wave into the tubular test object in the plurality of propagation directions are calculated based on the following equation (7) so that the respective internal refraction angles θk of the ultrasonic wave represented by the following equation (2) in the plurality of propagation directions are approximately equivalent, and the shape of the annular curved surface is determined so that the calculated angle of incidence θw is obtained:

$$\theta k = \cos^{-1}(\cos\theta r \cdot \cos\phi - \sin\theta r \cdot \cos\gamma \cdot \sin\phi) \quad (2)$$

where the external refraction angle θr, the propagation angle γ, and the angle φ in the above equation (2) are represented respectively by equations (7), (3), and (4):

$$\sin\theta r = Vs/Vi \cdot \sin\theta w \quad (7)$$

$$\gamma = \tan^{-1}\left(\frac{\sin\beta i}{\cos\beta i \cdot \sin\alpha i}\right) \quad (3)$$

$$\phi = \sin^{-1}(k \cdot \sin\theta') - \theta' \quad (4)$$

where, in the above equation (7), Vs means the propagation velocity of the ultrasonic wave propagated in the tubular test object, and Vi means the propagation velocity of the ultrasonic wave in the coupling medium filled between the ultrasonic probe and the tubular test object; and k and θ' in the above equation (4) are represented respectively by the following equations (5) and (6):

$$k = \frac{1}{1 - 2(t/D)} \quad (5)$$

$$\theta' = \cos\gamma \cdot \tan\theta r \quad (6)$$

where t/D in the above equation (5) means the ratio of thickness to outer diameter of the tubular test object.

Detection of the flaw in the tubular test object is generally performed by using an angle beam method using an ultrasonic shear wave. In the angle beam method, the ultrasonic wave is obliquely entered in the tubular test object at an angle equal to or larger than a longitudinal wave critical angle to cause total reflection of the ultrasonic longitudinal wave on the surface of the tubular test object and to propagate the ultrasonic shear wave in the tubular test object. At this point, the angle of refraction of the ultrasonic shear wave (angle of refraction of shear wave) needs to be about 35° or more. Therefore, when detecting the flaw in the tubular test object according to the method of the present invention, if the ultrasonic probe is arranged so as to face the tubular test object so that the longer axis is along the axial direction of the tubular test object, the shorter axis is along the circumferential direction of the tubular test object, and the center of the spheroid correctly faces the axial center of the tubular test object to be located in a vicinity of the external surface of the tubular test object, in order to reduce the ultrasonic longitudinal wave entering the tubular test object as much as possible, the shape of the annular curved surface may be determined so that at least the ultrasonic wave transmitted from the transducer located on the longer axis of the ultrasonic probe (transducer transmitting the ultrasonic wave which forms the largest angle of incidence or refraction angle with the tubular test object) is propagated into the tubular test object at the t angle of refraction of shear wave of 35° or more.

Therefore, preferably, in the step of arranging the ultrasonic probe so as to face the tubular test object, the ultrasonic probe is arranged so that the center of the spheroid correctly faces the axial center of the tubular test object and is located in a vicinity of an external surface of the tubular test object, and the shape of the annular curved surface is determined so that the ultrasonic wave transmitted from at least the transducer arranged on the longer axis of the ultrasonic probe among the plurality of transducers is propagated into the tubular test object at an angle of refraction of shear wave of 35° or more.

According to the preferable configuration, the ultrasonic wave transmitted at least from the transducer located on the longer axis of the ultrasonic probe (that is, the ultrasonic wave propagated in the axial direction of the tubular test object) can be propagated as the ultrasonic shear wave in the tubular test object.

To solve the above-described problems, the present invention is also provided, as an ultrasonic testing equipment for detecting a flaw by ultrasonic waves in a tubular test object, including: an ultrasonic probe arranged so as to face the tubular test object in which a plurality of transducers are arranged respectively in a row direction and a column direction in a matrix state on a plane or curved surface, and a transmission/reception control means for controlling transmission/reception of ultrasonic waves by the ultrasonic probe, wherein the transmission/reception control means selects a group of transducers including at least one transducer from the plurality of transducers and causes the selected one group of transducers to transmit and receive the ultrasonic wave in one propagation direction in the tubular test object, and selects another group of transducers including at least one transducer at a position different both in the row direction and column direction from that of any transducer constituting the one group of transducers and causes the another selected group of transducers to transmit and receive the ultrasonic wave in another propagation direction from the one propagation direction.

According to the invention, firstly one group of transducers including at least one transducer is selected from the plurality of transducers arranged in a matrix state by the transmission/reception control means and the ultrasonic wave is transmitted and received by the selected one group of transducers in one propagation direction of the tubular test object. Then, the flaw (hereinafter referred to as "first flaw") extending in the direction orthogonal to the one propagation direction will be detected by the ultrasonic wave transmitted and received in the one propagation direction. If the ultrasonic probe in which the plurality of transducers are arranged in a matrix state on the curved surface is adopted, the direction in which the ultrasonic wave is transmitted and received by each transducer is determined by a radius of curvature of the curved surface and a position of each transducer, and so the group of transducers capable of transmitting and receiving the ultrasonic wave in the one propagation direction may simply be selected from the plurality of transducers. If the ultrasonic probe in which the plurality of transducers are arranged in a matrix state on the plane is adopted, on the other hand, a configuration that controls transmission/reception time-shift of the ultrasonic wave by each transducer constituting the selected one group of transducers can be adopted so that the ultrasonic wave is transmitted and received by the selected one group of transducers in the one propagation direction.

Next, according to the present invention, by the transmission/reception control means, another group of transducers including at least one transducer on a position different both in the row direction and column direction from that of the transducer constituting the one group of transducers is selected from the plurality of transducers arranged in a matrix state and the ultrasonic wave is transmitted and received by the selected another group of transducers in another propagation direction different from the one propagation direction of the tubular test object. By the ultrasonic wave transmitted and received in the another propagation direction, the flaw (hereinafter referred to as "second flaw") extending in the direction orthogonal to the another propagation direction will be detected. Since the another group of transducers includes the transducer whose position in the row and column directions is different from that of the transducer constituting the one group of transducers, not only the propagation direction of the ultrasonic wave is changed from the one propagation direction to the another propagation direction, but also the position along the circumferential direction of the tubular test object of the group of transducers transmitting and receiving the ultrasonic wave is also changed simultaneously. Therefore, by setting change amount of the position appropriately, the propagation directions of the ultrasonic waves for both the first flaw and the second flaw can be made orthogonal to each other, while at the same time the external refraction angles θr and/or the internal refraction angles θk can be made to be approximately constant, so that it becomes possible to obtain equivalent echo intensity regardless of the tilt angle of each flaw. By selecting the number of groups of transducers equal to the number of propagation directions of the ultrasonic wave and setting up each of the selected groups of transducers to transmit and receive the ultrasonic wave, as described above, the flaws with various tilt angles in accordance with the number of the propagation directions can be detected with high precision.

By adopting a configuration in which the ultrasonic wave is transmitted and received by each of the selected groups of transducers approximately simultaneously, the flaws with various tilt angles can be quickly detected.

As described above, the ultrasonic testing equipment according to the present invention can quickly detect the flaws with various tilt angles with respect to the axial direction of the tubular test object with high precision.

A time required for the ultrasonic wave transmitted by each selected group of transducers to enter the tubular test object depends on a distance between each group of transducers and the incident point of the ultrasonic wave. Since the distance between each group of transducers and the incident point of the ultrasonic wave depends on shapes of the ultrasonic probe and the tubular test object, timing when the ultrasonic wave actually enters the tubular test object and reception timing of the surface echo on the surface (internal and external surfaces) of the tubular test object will be different even if the ultrasonic wave is transmitted with a same timing from each selected group of transducers. Thus, if the echoes received by the respective groups of transducers are synthesized and the flaws are detected based on a pertinent synthesized echo, the surface echoes on the surface (internal and external surfaces) of the tubular test object received by the respective groups of transducers may be continuous or partly overlapped due to different incidence timing of the ultrasonic waves transmitted from the respective groups of transducers, and as a result of broadened width of the overall echoes on the surface of the tubular test object, there is a danger of an increasing dead zone in the vicinity of the external and internal surfaces of the tubular test object.

To avoid such a problem, the transmission/reception control means controls transmission time-shift or reception time-shift of the ultrasonic waves of the one group of transducers and the another group of transducers so that a surface echo on the tubular test object of the ultrasonic wave transmitted from the one group of transducers and another surface echo on the tubular test object of the ultrasonic wave transmitted from the another group of transducers are received at approximately the same time.

According to the preferable invention, since transmission time-shift or reception time-shift of the ultrasonic waves of the one group of transducers and the another group of transducers is controlled so that a surface echo on the tubular test object of the ultrasonic wave transmitted from the one group of transducers and another surface echo on the tubular test object of the ultrasonic wave transmitted from the another group of transducers are received at approximately the same time (so that a time difference is equal to or less than a pulse width of the transmitted ultrasonic wave, for example), the dead zone in the vicinity of the external and internal surfaces of the tubular test object can be reduced even if a configuration in which the echoes received by the respective groups of transducers are synthesized and the flaw is detected based on a pertinent synthesized echo is adopted.

To solve the above problem, the present invention is also provided as an ultrasonic probe for detecting a flaw by ultrasonic waves in a tubular test object, including a plurality of transducers arranged along an annular curved surface, wherein the annular curved surface is obtained by cutting a predetermined spheroid with two parallel planes facing to each other that do not pass through a center of the spheroid and do not sandwich the center of the spheroid, said two parallel planes being orthogonal to the rotational axis of the spheroid.

According to the ultrasonic probe, since the plurality of transducers are arranged along the annular curved surface obtained by cutting the predetermined spheroid with two parallel planes facing to each other that do not pass through the center of the spheroid and do not sandwich the center of the spheroid, said two parallel planes being orthogonal to the rotational axis of the spheroid, the ultrasonic wave transmitted by each transducer will be propagated toward the center of the spheroid. Then, the ultrasonic probe according to the present invention is arranged so as to face the tubular test object so that the longer axis direction is along the axial direction of the tubular test object, the shorter axis direction is along the circumferential direction of the tubular test object, and the center of the spheroid correctly faces the axial center of the tubular test object, the transducers for transmitting the ultrasonic waves should be selected (as many transducers as the number of tilt angles of the flaws to be detected are selected) so that, for example, the direction in which the flaws with a predetermined tilt angle to be detected extend and the propagation direction of the ultrasonic wave are orthogonal to each other. Since, at this point, an elevation angle of each transducer viewed from the center of the spheroid is different depending on the position where each transducer is arranged, the angle of incidence of the ultrasonic wave transmitted from each transducer with the tubular test object will also be different. Therefore, by setting the shape (annular curved surface shape) of the ultrasonic probe appropriately, it becomes possible to cause the propagation direction of the ultrasonic wave transmitted from each transducer and the extension direction of the flaw to be detected are orthogonal to each other and, at the same time, to maintain the external refraction angle $\theta r$ and/or the internal refraction angle $\theta k$ approximately constant, so that equivalent echo intensity can be obtained regardless of the tilt angle of each flaw. By selecting as many transducers as the number of propagation directions of ultrasonic waves and adopting a configuration in which ultrasonic waves are transmitted and received by each of the selected transducers, as described above, flaws with various tilt angles can be detected with high precision.

By transmitting and receiving the ultrasonic wave approximately simultaneously by each of the selected transducers, the flaws with various tilt angles can be quickly detected.

As described above, the ultrasonic probe according to the present invention can quickly detect the flaws with various tilt angles with respect to the axial direction of the tubular test object with high precision.

Preferably the ultrasonic probe further includes at least one straight beam probe arranged along a straight line that passes through the center of the spheroid and is orthogonal to the two parallel planes.

According to the preferable invention, since, in addition to the ultrasonic testing (angle beam method) by the plurality of transducers arranged along the annular curved surface, a normal beam method by the straight beam probe (ultrasonic probe capable of causing the ultrasonic wave to enter orthogonally to the external surface of the tubular test object) can be applied, thickness measurement of the tubular test object, detection of lamination and the like can advantageously be performed, simultaneously with the angle beam method of the tubular test object.

To solve the above problem, the present invention is also provided as an ultrasonic testing equipment including: the ultrasonic probe arranged so as to face the tubular test object so that a longer axis direction of the ultrasonic probe is along an axial direction of the tubular test object, a shorter axis direction of the ultrasonic probe is along a circumferential direction of the tubular test object, and the center of the spheroid correctly faces an axial center of the tubular test object; and a transmission/reception control means for controlling transmission/reception of ultrasonic waves by the ultrasonic probe, wherein the transmission/reception control means causes at least two transducers among the plurality of transducers to transmit the ultrasonic waves to and receive the same from the tubular test object.

According to the invention, the transmission/reception control means selects as many transducers as the number of the propagation directions of the ultrasonic waves (number of tilt angles of the flaws to be detected) and causes each selected transducer to transmit and receive the ultrasonic wave, the flaws with various tilt angles can quickly be detected with high precision.

If the ultrasonic probe is arranged so that the center of the spheroid is outside the vicinity of the external surface of the tubular test object, the incident point of the ultrasonic wave transmitted by each transducer into the tubular test object is different in each transducer. Therefore, under an assumption that the ultrasonic probe is arranged so that the center of the spheroid is located in the vicinity of the external surface of the tubular test object, even if the propagation direction of the ultrasonic wave transmitted from each transducer and the extension direction of the flaw to be detected are caused to be orthogonal to each other and, at the same time, the shape (shape of the annular curved surface) of the ultrasonic probe is determined so that the external refraction angle and/or internal refraction angle are maintained approximately constant, planned propagation behavior of the ultrasonic wave cannot be obtained (non-constant external refraction angle and/or internal refraction angle in accordance with the propagation direction of the ultrasonic wave), particularly when the tubular test object has a small diameter (100 mm or less in outer diameter), due to the different incident point of the ultrasonic wave on the tubular test object, thereby causing, as a result, a concern about reduced detectability of the flaw.

Therefore, preferably, the ultrasonic probe is arranged so that the center of the spheroid is located in a vicinity of an external surface of the tubular test object.

According to the preferable configuration, since the incident points of the ultrasonic waves transmitted by the respective transducers on the tubular test object approximately agree, the planned propagation behavior of the ultrasonic waves can be obtained (approximately constant external refraction angle and/or internal refraction angle regardless of the propagation directions of the ultrasonic waves) and, as a result, the flaws with various tilt angles can be detected with high precision.

Preferably the transmission/reception control means controls transmission time-shift or reception time-shift of the ultrasonic waves of one transducer and another transducer among at least two transducers that transmit the ultrasonic waves to and receive the same from the tubular test object, so that a surface echo on the tubular test object of the ultrasonic wave transmitted from the one transducer and another surface echo on the tubular test object of the ultrasonic wave transmitted from the another transducer are received at approximately the same time.

According to the preferable configuration, since transmission time-shift or reception time-shift of the ultrasonic waves of the one transducer and the another transducer is controlled so that a surface echo on the tubular test object of the ultrasonic wave transmitted from the one transducer and another surface echo on the tubular test object of the ultrasonic wave transmitted from the another transducer are received at approximately the same time (so that the time difference is equal to or less than the pulse width of the transmitted ultrasonic wave, for example), the dead zone in the vicinity of the external and internal surfaces of the tubular test object can be reduced even if the configuration in which the echoes received by the respective transducers are synthesized and the flaw is detected based on a pertinent synthesized echo is adopted.

If the propagation direction of the ultrasonic wave transmitted from each transducer constituting the ultrasonic probe and the extension direction of the flaw to be detected are caused to be orthogonal to each other and, at the same time, the shape (shape of the annular curved surface) of the ultrasonic probe is set so that the external refraction angle and/or the internal refraction angle are maintained approximately constant, an appropriate shape of the ultrasonic probe is different depending on the ratio of thickness to outer diameter of the tubular test object and the like, and once the shape is set, the angle of incidence of the ultrasonic wave transmitted from each transducer has a fixed value for each transducer. Therefore, there is a problem in cost and maintainability because the ultrasonic probes in appropriate shapes must be prepared individually for the tubular test objects with various ratios of thickness to outer diameter.

Therefore, preferably, an adjustment means for adjusting an angle of incidence of the ultrasonic wave transmitted from each of the plurality of transducers to the tubular test object is provided.

According to the preferable configuration, since the angle of incidence of the ultrasonic wave transmitted to the tubular test object from each of the plurality of transducers can be fine-tuned so that the propagation direction of the ultrasonic wave transmitted from each transducer and the extension direction of the flaw to be detected can be made to be orthogonal to each other, while at the same time, the external refraction angle and/or the internal refraction angle can be made to be approximately constant even if the ultrasonic probe have the same shape, there is no need to prepare ultrasonic probes in various shapes, and thus an advantage in cost and maintainability can be gained.

As the adjustment means, for example, a mechanical declination mechanism can be adopted. In addition, it is possible that each of the plurality of transducers has a plurality of piezoelectric elements divided into a rectangular shape along a radial direction of each transducer, and the adjustment means adjusts the angle of incidence of the ultrasonic wave transmitted to the tubular test object by electrically controlling transmission/reception time-shift of the ultrasonic wave by the plurality of piezoelectric elements.

According to the preferable invention, compared with a case of adopting the mechanical declination mechanism, the angle of incidence can be adjusted more easily with improved reproducibility.

Preferably the ultrasonic testing equipment includes a follow-up apparatus for maintaining a relative position of the ultrasonic probe with respect to the tubular test object approximately constant in a plane orthogonal to the axial direction of the tubular test object.

According to the preferable invention, when performing ultrasonic testing by relatively rotating the ultrasonic probe along the circumferential direction of the tubular test object and relatively moving the same along the axial direction of the tubular test object, the relative position of the ultrasonic probe with respect to the tubular test object can be maintained approximately constant by the follow-up apparatus, even if the tubular test object has the cross sectional shape which is not a complete round or in which an axial bend is occurred. Therefore, according to the above preferable configuration, even if the ultrasonic probe is relatively rotated with respect to the tubular test object or is moved along the axial direction thereof, variations in the angle of incidence of the ultrasonic wave on the tubular test object from each transducer are suppressed and, as a result, detectability of the flaw can be maintained approximately constant.

As the follow-up apparatus, a follow-up apparatus using a contact-type displacement gauge or a follow-up apparatus constructed from contact-type mechanical components such as saddle shoes may be adopted. However, if such follow-up apparatuses are adopted, problems shown below may arise:

(1) When the contact-type displacement gauge or the contact-type mechanical component is brought into contact with the external surface of the tubular test object or removed from the external surface at front and rear ends of the tubular test object, shakiness tends to appear. Thus, tracking at the front and rear ends of the tubular test object tends to decrease.

(2) If the contact-type follow-up apparatus is used, even slight unevenness on the external surface of the tubular test object may decrease tracking (too sensitive to uneven property of the external surface of the tubular test object).

(3) Repeated use leads to wear of the contact-type displacement gauge or contact-type mechanical component, resulting in reduced tracking (frequent maintenance is needed).

Then, due to the above decrease in tracking of (1) to (3), detectability of the flaw may also be reduced.

Therefore, preferably, the follow-up apparatus includes one or more non-contact displacement gauges for measuring a distance up to the external surface of the tubular test object, a positioning mechanism for moving the ultrasonic probe along two directions orthogonal to the axial direction of the tubular test object and a positioning control means for controlling the positioning mechanism; and the positioning control means controls the positioning mechanism based on the distance measured by the non-contact displacement gauges so that the relative position of the ultrasonic probe with respect to the tubular test object is approximately constant.

According to the preferable invention, since the positioning mechanism is controlled (the position of the ultrasonic probe is adjusted), based on the distance up to the ultrasonic probe and the external surface of the tubular test object calculated using the non-contact displacement gauge that is not in contact with the tubular test object, so that the relative position of the ultrasonic probe with respect to the tubular test object is approximately constant, compared with the above case where the contact-type displacement gauge is adopted, better tracking can be obtained and, as a result, excellent detectability of the flaw can be obtained.

Also, to solve the above problem, the present invention is also provided as an ultrasonic testing method wherein, using the ultrasonic testing equipment, a flaw in all or part of the tubular test object is detected by relatively rotating the ultrasonic probe along the circumferential direction of the tubular test object and relatively moving the same along the axial direction of the tubular test object.

Furthermore, to solve the above problem, the present invention is also provided as a manufacturing method of a seamless pipe or tube including: a first process of manufacturing a seamless pipe or tube by piercing a billet; and a second process of detecting a flaw in the seamless pipe or tube manufactured in the first process by using the ultrasonic testing method.

BRIEF DESCRIPTION OF THE DRAWINGS

FIG. 4 (a) shows a perspective view, FIG. 4 (b) shows a sectional view in a circumferential direction of a pipe, FIG. 4 (c) shows a sectional view in an axial direction of the pipe, and FIG. 4 (d) shows a sectional view along a propagation plane of ultrasonic waves.

FIG. 5 (a) shows a perspective view, FIG. 5 (b) shows a plan view, FIG. 5 (c) shows a side view, and FIG. 5 (d) shows an illustration.

FIG. 6 (a) shows a perspective view, FIG. 6 (b) shows a sectional view in the circumferential direction of a pipe, FIG. 6 (c) shows a plan view, and FIG. 6 (d) shows a sectional view along the propagation plane of ultrasonic waves.

FIG. 12 (a) shows a front sectional view, FIG. 12 (b) shows a plan view, and FIG. 12 (c) shows a side sectional view.

BEST MODE FOR CARRYING OUT THE INVENTION

Embodiments of the present invention will be described with reference to attached drawings when deemed appropriate by taking cases where embodiments are applied to pipes such as steel pipes as examples.

First Embodiment

Figure 1:
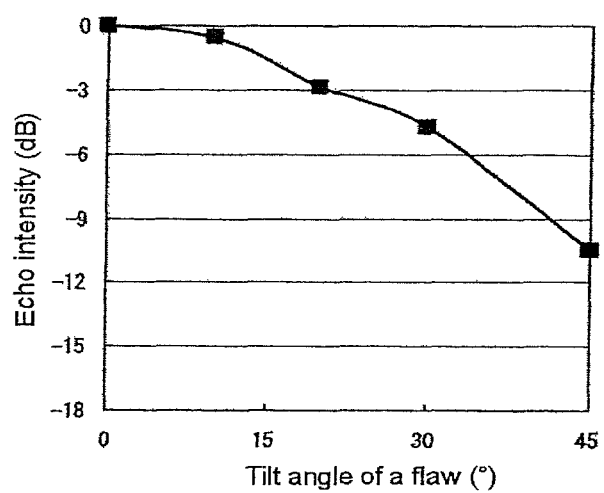
FIG. 1 is a diagram illustrating a relation between a tilt angle of tilted flaws and echo intensity by a ultrasonic testing method applying a conventional ultrasonic phased array probe.
Figure 2:
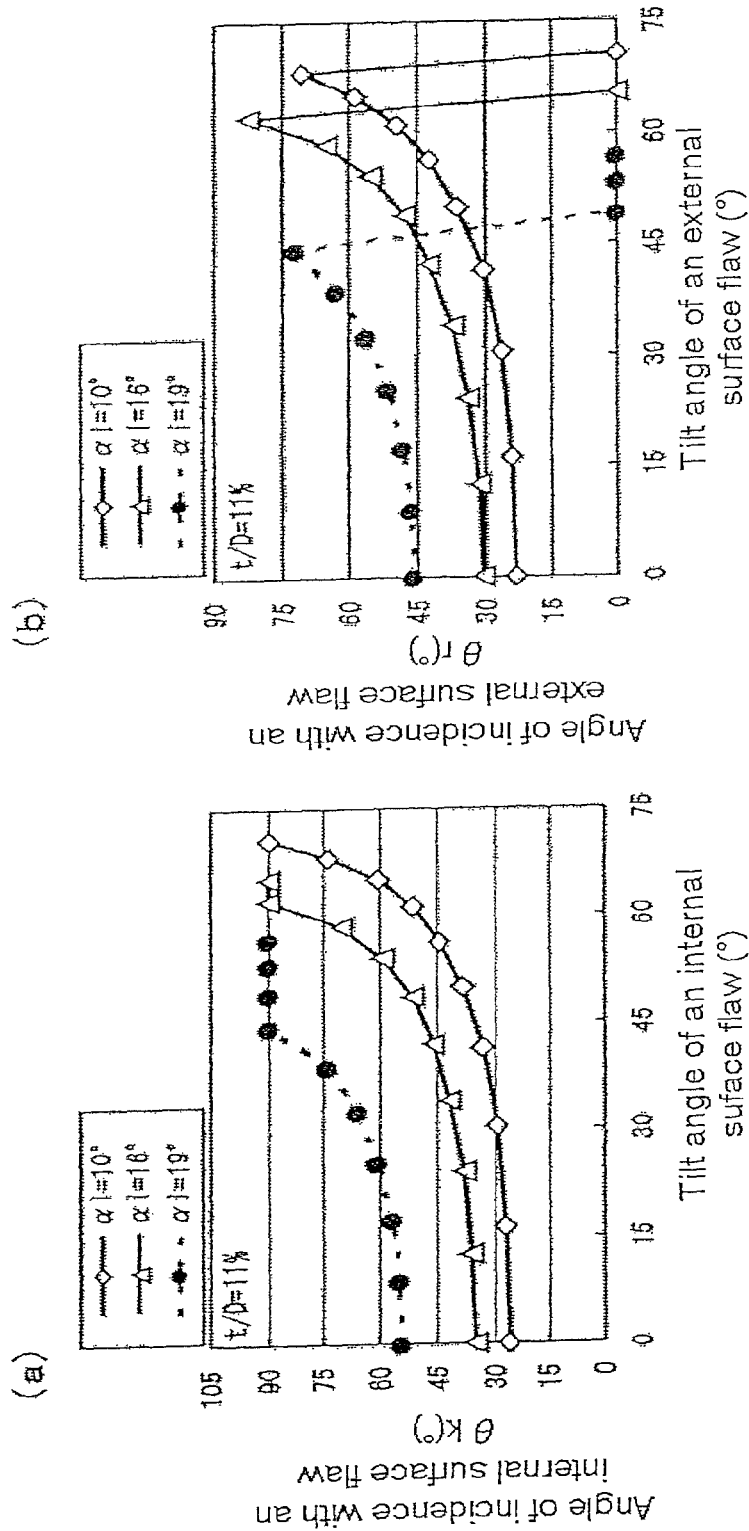
FIG. 2(a) and FIG. 2(B) show diagrams illustrating relations between the tilt angle of tilted flaws and an angle of incidence of an ultrasonic wave with the tilted flaws by the ultrasonic testing method applying a conventional ultrasonic phased array probe.
Figure 3:
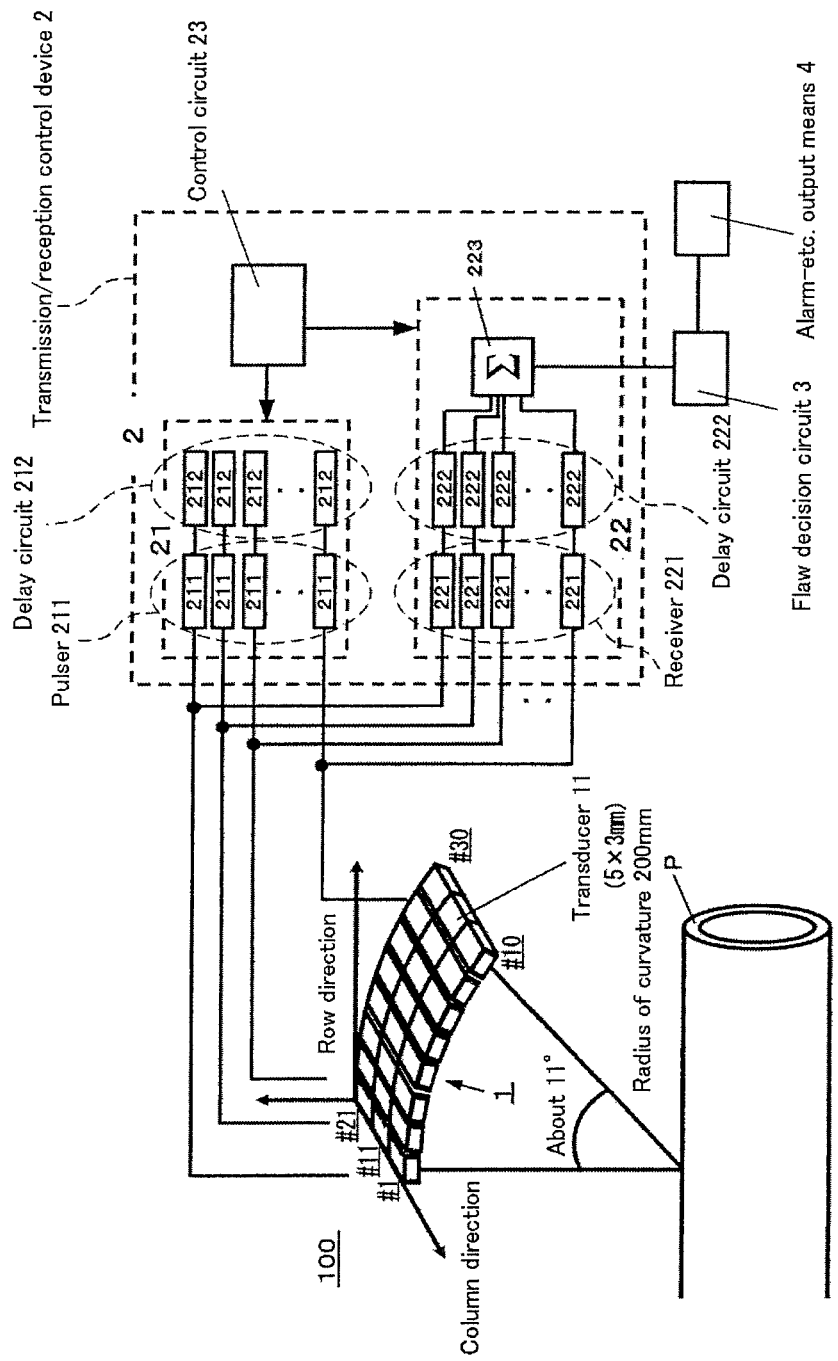
FIG. 3 is a schematic diagram showing an outline configuration of an ultrasonic testing equipment according to the first embodiment of the present invention.
Figure 4:
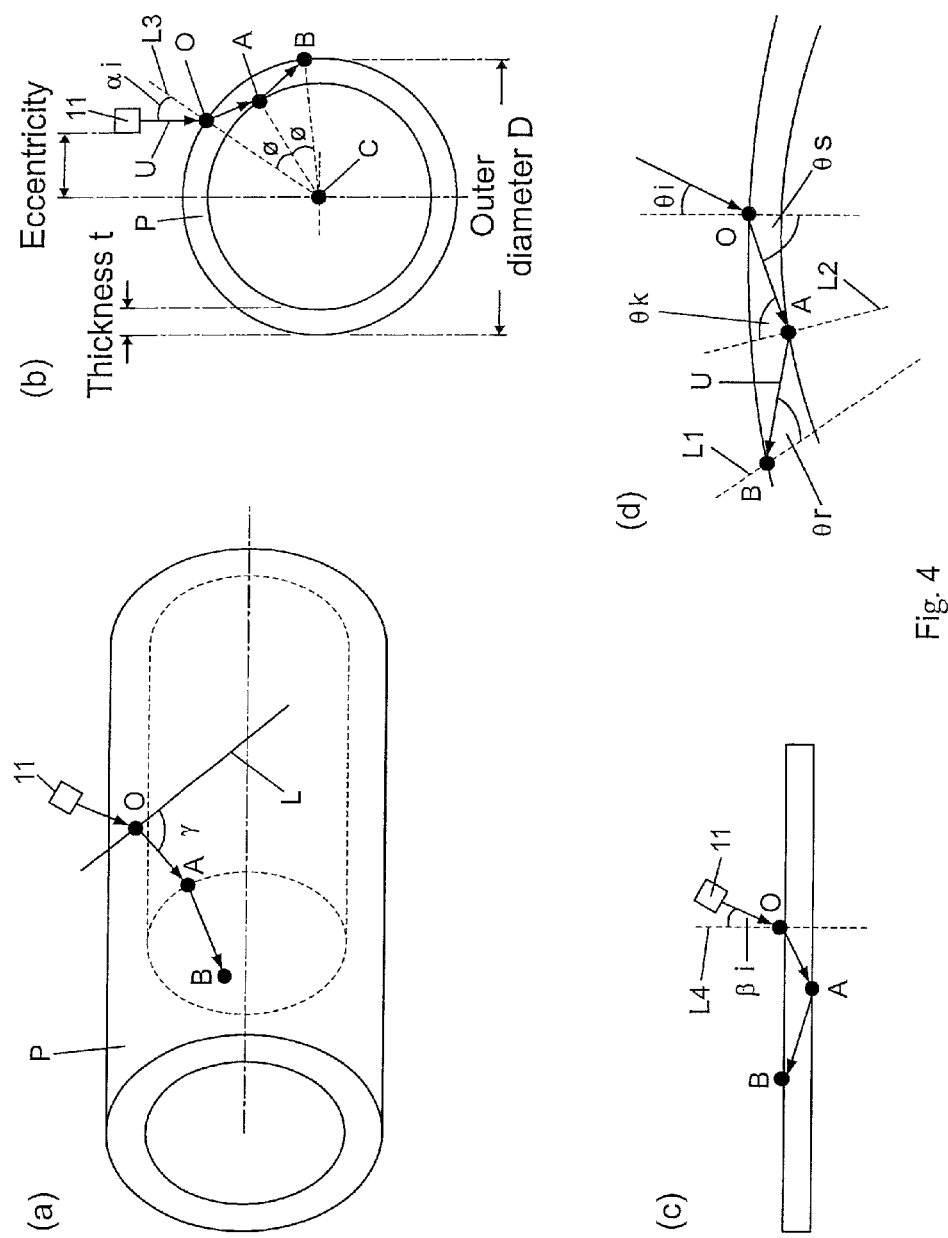
FIG. 4 is an illustration showing propagation behavior of an ultrasonic wave in the ultrasonic testing equipment shown in FIG. 3.

FIG. 3 is a schematic diagram showing an outline configuration of an ultrasonic testing equipment according to the first embodiment of the present invention, and FIG. 2 is an illustration showing propagation behavior of an ultrasonic wave in the ultrasonic testing equipment shown in FIG. 3. FIG. 4 (a) shows a perspective view, FIG. 4 (b) shows a sectional view in a circumferential direction of a pipe, FIG. 4 (c) shows a sectional view in an axial direction of a pipe, and FIG. 4 (d) shows a sectional view along a propagation plane (plane containing points O, A, and B shown in FIG. 4 (a)) of ultrasonic waves. As shown in FIG. 3, an ultrasonic testing equipment 100 according to the present embodiment is an ultrasonic testing equipment for detecting a flaw in a pipe P having an ultrasonic probe 1 in which a plurality of transducers 11 are arranged in a row direction and a column direction respectively in a matrix state (arranged on a cylinder curved in the row direction in a matrix state in the example shown in FIG. 3) on a plane or curved surface, and a transmission/reception control means 2 for controlling transmission/reception of an ultrasonic wave by the ultrasonic probe 1. Also, the ultrasonic testing equipment 100 according to the present embodiment has a flaw decision circuit 3 for detecting flaws existing in the pipe P by comparing an amplitude of an echo (more concretely, an echo synthesized by a waveform synthesis circuit 223 described later) from the pipe P with a predetermined threshold and an alarm-etc. output means 4 for outputting a predetermined warning or the like when a flaw is detected by the flaw decision circuit 3.

The ultrasonic probe 1 is arranged so as to face the pipe P so that the row direction is along an axial direction of the pipe P and the column direction is along a circumferential direction of the pipe P.

The transmission/reception control means 2 according to the present embodiment has a transmission circuit 21, a reception circuit 22, and a control circuit 23. The transmission circuit 21 has a pulser 211 connected to each transducer 11 to supply a pulse signal to cause each transducer 11 to transmit an ultrasonic wave and a delay circuit 212 for setting a delay time for a pulse signal to be supplied to each transducer 11 from each pulser 211. The reception circuit 22 has a receiver 221 connected to each transducer 11 to amplify an echo received by each transducer 11, a delay circuit 222 for setting a delay time for an echo amplified by each receiver 221, and a waveform synthesis circuit 223 for synthesizing an echo to which a delay time is set by each delay circuit 222. The control circuit 23 operates to select, from among a plurality of arranged transducers 11, transducers 11 for transmitting and receiving an ultrasonic wave and also to determine a delay time set by the delay circuit 212 or the delay circuit 222 for each selected transducer 11.

The transmission/reception control means 2 (control circuit 23) having the above configuration selects, from among a plurality of transducers 11 arranged in a matrix state, a group of transducers composed of one or more transducers 11 including an transducer 11 arranged in a predetermined column to cause the selected group of transducers to transmit and receive an ultrasonic wave in a direction forming a predetermined angle with respect to the axial direction of the pipe P and selects, from among a plurality of transducers 11 arranged in a matrix state, a different group of transducers composed of one or more transducers 11 including another transducer 11 arranged in a different column from that of the above transducer 11 with a different center of gravity in a column direction from that of the above group of transducers to cause the selected another group of transducers to transmit and receive an ultrasonic wave in a direction forming a different angle from the predetermined angle with respect to the axial direction of the pipe P.

Operations of the transmission/reception control means 2 (control circuit 23) will be described below more concretely with reference to FIG. 4 when deemed appropriate. As shown in FIG. 4, an ultrasonic wave transmitted by each transducer 11 constituting the ultrasonic probe 1 enters the pipe P through point O on an external surface of the pipe P and is reflected at point A on an internal surface of the pipe P before reaching point B on the external surface of the pipe P. Then, if an angle (propagation angle) formed by the propagation direction of the ultrasonic wave that entered the pipe P through point O (propagation direction viewed from the normal direction of a tangential plane of the pipe P including the incident point O) and a circumferential tangent L of the pipe P passing through the incident point O is γ (hereinafter called also as "propagation direction γ"), the external refraction angle (angle formed by a normal L1 at point B of the pipe P and an ultrasonic wave beam U in a propagation plane of ultrasonic waves shown in FIG. 4 (d)) at point B is θr, and the internal refraction angle (angle formed by a normal L2 at point A of the pipe P and the ultrasonic wave beam U in the propagation plane of ultrasonic waves shown in FIG. 4 (d))) at point A is θk, θr, θk, and γ are represented by the following equations (1) to (3).

$$\theta r = \sin^{-1}\left(\{(Vs/Vi)^2 \cdot (\sin^2\beta i + \cos^2\beta i \cdot \sin^2\alpha i)\}^{1/2}\right) \quad (1)$$

$$\theta k = \cos^{-1}(\cos\theta r \cdot \cos\phi - \sin\theta r \cdot \cos\gamma \cdot \sin\phi) \quad (2)$$

$$\gamma = \tan^{-1}\left(\frac{\sin\beta i}{\cos\beta i \cdot \sin\alpha i}\right) \quad (3)$$

where, in the above equations (1) and (3), αi means a circumferential angle of incidence (angle formed by a normal L3 at point O of the pipe P and the ultrasonic wave beam U in a circumferential cross section of the pipe, see FIG. 4 (b)) of an ultrasonic wave into the pipe P and βi means an axial angle of incidence (angle formed by a normal L4 at point O of the pipe P and the ultrasonic wave beam U in an axial cross section of the pipe, see FIG. 4 (c))) of an ultrasonic wave into the pipe P. In the above equation (1), Vs means the propagation velocity of an ultrasonic wave propagating in the pipe P and Vi means the propagation velocity of an ultrasonic wave in a coupling medium filled between the transducer 11 and the pipe P. Furthermore, in the above equation (2), φ means, in the axial cross section of the pipe shown in FIG. 4 (b), an angle formed by a straight line passing through a pipe center C and point O and a straight line passing through the pipe center C and point A (equal to an angle formed by a straight line passing through the pipe center C and point A and a straight line passing through the pipe center C and point B) and is represented by the following equation (4).

$$\phi = \sin^{-1}(k \cdot \sin \theta') - \theta' \quad (4)$$

Then, in the above equation (4), k and θ' are represented by the following equations (5) and (6).

$$k = \frac{1}{1 - 2(t/D)} \quad (5)$$

$$\theta' = \cos\gamma \cdot \tan\theta r \quad (6)$$

According to the above equations (1) and (3), the external refraction angle θr and the propagation velocity γ of an ultrasonic wave are determined by the circumferential angle of incidence αi of an ultrasonic wave into the pipe P and the axial angle of incidence βi of an ultrasonic wave into the pipe P. Also, by using the above equations (1) to (6), the internal refraction angle θk is also determined by the circumferential angle of incidence αi and the axial angle of incidence βi (however, strictly, φ determined by the ratio of thickness to outer diameter of the pipe P is effective.).

According to the method described in Patent Literature 2 as described above, if an ultrasonic probe is arranged with a constant eccentricity from the axial center of the pipe P (that is, the circumferential angle of incidence αi into the pipe P determined in accordance with the eccentricity is maintained constant), only the tilt angle of an ultrasonic wave with respect to the axial direction of the pipe P is changed (only the axial angle of incidence βi is changed) so that the propagation direction of the ultrasonic wave and the extension direction of the tilted flaw are orthogonal to each other. While being derived from the above equations (1) and (2), in the method in which only the axial angle of incidence βi is changed, echo intensity changes depending on the propagation direction of an ultrasonic wave (depending on the tilt angle of the tilted flaw), as in the finding of the present inventors described above, because the external refraction angle θr and the internal refraction angle θk respectively change depending on change in the axial angle of incidence βi and, as a result, detectability of the flaw changes.

In contrast, in the ultrasonic testing equipment 100 according to the present embodiment, as described above, the transmission/reception control means 2 (control circuit 23) operates first to select, from among a plurality of transducers 11 arranged in a matrix state, a group of transducers including at least one transducer 11 and to cause the selected group of transducers to transmit and receive an ultrasonic wave in a propagation direction γ in the pipe P. More concretely, the control circuit 23 determines the circumferential angle of incidence αi and the axial angle of incidence βi based on the above equation (3) so that the propagation direction γ of an ultrasonic wave meeting orthogonal to the extension direction of flaws with a predetermined tilt angle to be detected (first flaws) can be obtained and then selects a group of transducers that provide the determined αi and βi.

Next, the transmission/reception control means 2 (control circuit 23) operates to select, from among a plurality of transducers 11 arranged in a matrix state, another group of transducers including at least one transducer 11 from a position that is different both in the row and column directions from that of the transducer 11 constituting the above group of transducers and to cause the selected another group of transducers to transmit and receive an ultrasonic wave in another propagation direction γ different from the above propagation direction γ in the pipe P. More concretely, the control circuit 23 determines the circumferential angle of incidence αi and the axial angle of incidence βi based on the above equation (3) so that the propagation direction γ of an ultrasonic wave meeting orthogonal to the extension direction of flaws (second flaws) with a tilt angle to be detected that is different from that of the first flaws can be obtained and then selects a group of transducers that provide the determined αi and βi. Since, at this point, the another group of transducers includes transducers whose position in the row and column direction is different from that of transducers constituting the one group of transducers, the circumferential angle of incidence αi of an ultrasonic wave transmitted and received by the one group of transducers will be different from that of an ultrasonic wave transmitted and received by the another group of transducers. Since the propagation direction γ of an ultrasonic wave of the one group of transducers and that of an ultrasonic wave of the another group of transducers are different, the axial angle of incidence βi of an ultrasonic wave of the transmitted and received by the one group of transducers will be different from that of an ultrasonic wave transmitted and received by the another group of transducers. Still more concretely, when selecting the another group of transducers, the circumferential angle of incidence αi and the axial angle of incidence βi of the another group of transducers are determined so that the circumferential angle of incidence and the axial angle of incidence are different from those of the one group of transducers (αi and βi so that a propagation direction γ of an ultrasonic wave meeting orthogonal to the extension direction of second flaws based on the equation (3) can be obtained) and both the external refraction angle θr determined by the above equation (1) and internal refraction angle θk determined by the above equation (2) are approximately equivalent to θr and θk of the one group of transducers respectively, and then each transducer 11 in the another group of transducers is selected so that the pertinent αi and βi are obtained.

With the operations of the transmission/reception control means 2 (control circuit 23) described above, the propagation direction γ of an ultrasonic wave can be caused to are orthogonal to each other with both the first and second flaws and, at the same time, refraction angles (θr, θk) can be made to be approximately equivalent so that equivalent echo intensity can be obtained regardless of the tilt angle of each flaw. By selecting as many groups of transducers as the number of tilt angles of flaws to be detected and causing each selected group of transducers to transmit and receive an ultrasonic wave, as described above, flaws with various tilt angles can be detected with high precision. Also, an ultrasonic wave is transmitted and received by each selected group of transducers approximately simultaneously, flaws with various tilt angles can quickly be detected.

In the ultrasonic testing equipment 100 according to the present embodiment, the axial angle of incidence βi of an ultrasonic wave transmitted and received by each transducer 11 is determined by the radius of curvature of a curved surface and the position of each transducer 11 because the ultrasonic probe 1 in which transducers are arranged on the curved surface in a matrix state (arranged on a cylinder curved in the row direction in a matrix state) is used. Therefore, when selecting a group of transducers, a group of transducers that provide a determined axial angle of incidence βi can simply be selected from among a plurality of transducers 11. However, the present invention is not limited to this and an ultrasonic probe in which a plurality of transducers 11 are arranged on a plane in a matrix state can also be adopted. In this case, transmission/reception time-shift of an ultrasonic wave by each transducer 11 in a selected group of transducers may be controlled by the control circuit 23 so that an ultrasonic wave is transmitted and received by the selected group of transducers in the determined axial angle of incidence βi.

In the ultrasonic testing equipment 100 according to the present embodiment, as described above, in order to simplify the circuit configuration to reduce the manufacturing cost, an echo received by each transducer 11 is synthesized by the waveform synthesis circuit 223 and, based on the synthesized echo, flaws are detected by the flaw decision circuit 3. With such an apparatus, the transmission/reception control means 2 (control circuit 23) according to the present embodiment controls, as a preferable configuration, transmission timeshift or reception time-shift of ultrasonic waves of the one group of transducers and the another group of transducers (a delay time of the corresponding delay circuit 212 or the delay circuit 222 is set) so that a surface echo on a pipe P of an ultrasonic wave transmitted by the one group of transducers and another surface echo on the pipe P of an ultrasonic wave transmitted by the another group of transducers are received at approximately the same time (so that a time difference is equal to or less than a pulse width of a transmitted ultrasonic wave, for example).

Since, with such a preferable apparatus, surface echo on the pipe P of an ultrasonic wave transmitted by the one group of transducers and another surface echo on the pipe P of an ultrasonic wave transmitted by the another group of transducers are received at approximately the same time, even if an echo received by each transducer 11 (each group of transducers) is synthesized by the waveform synthesis circuit 223, as described above, a circumstance, in which a width of overall echoes is broadened because surface echoes on the pipe surfaces (internal and external surfaces) received by each group of transducers are continuous or partly overlapped, can hardly occur, and thus a dead zone in the vicinity of internal and external surfaces of the pipe P can be reduced.

Second Embodiment

Figure 5:
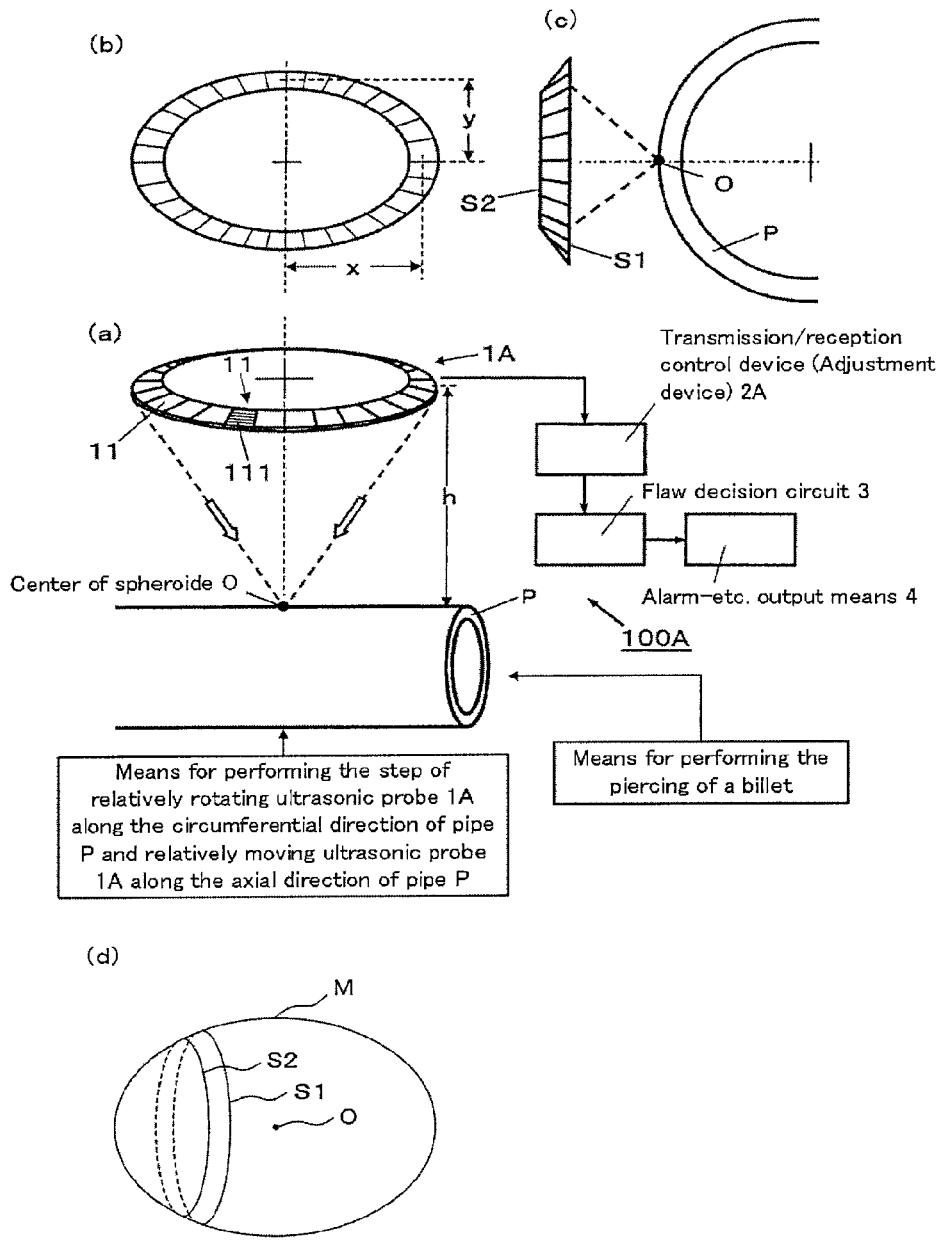
FIG. 5 is a schematic diagram showing the outline configuration of an ultrasonic testing equipment according to the second embodiment of the present invention.
Figure 6:
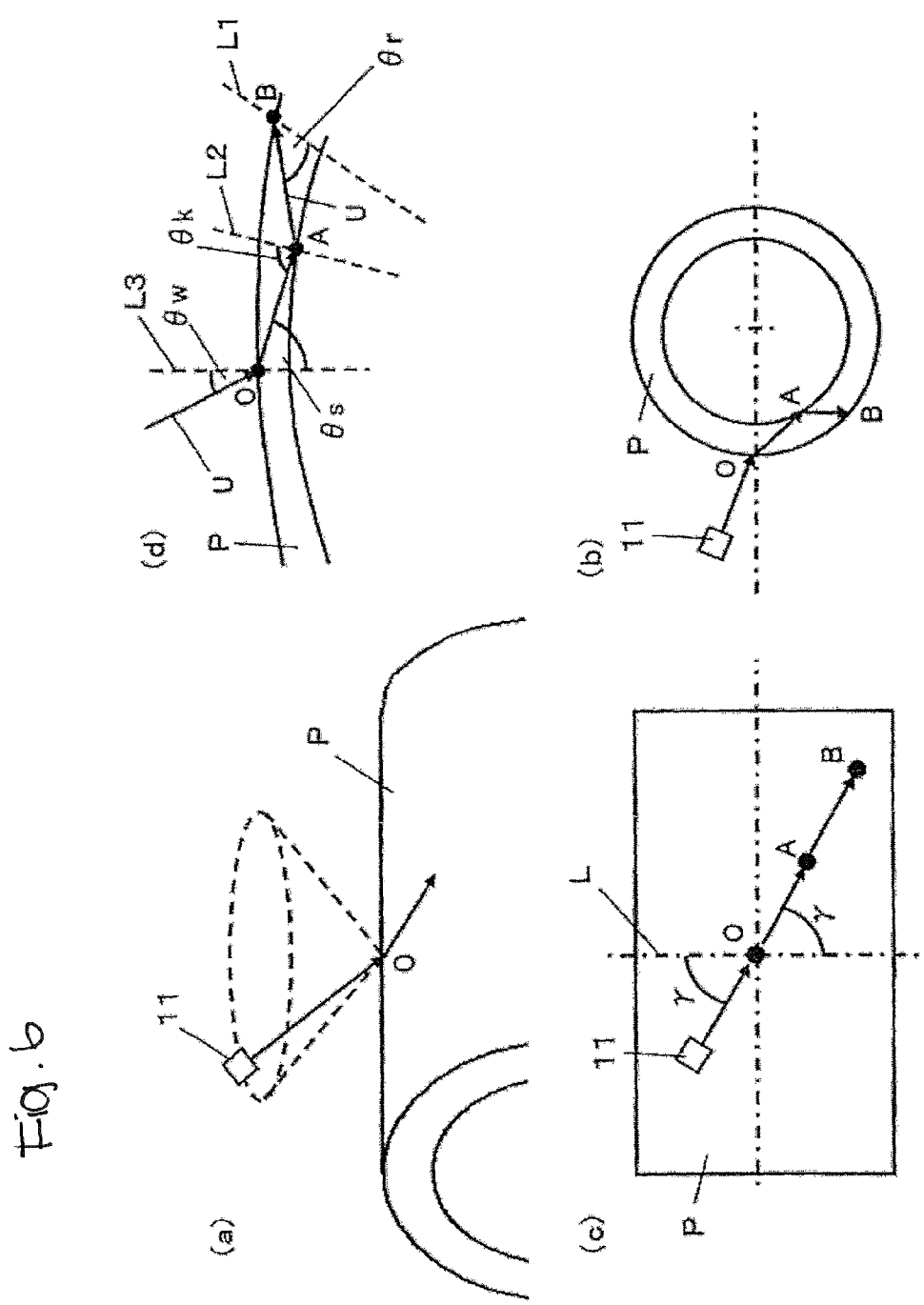
FIG. 6 is an illustration showing propagation behavior of an ultrasonic wave in the ultrasonic testing equipment shown in FIG. 5.

FIG. 5 is a schematic diagram showing the outline configuration of an ultrasonic testing equipment according to the second embodiment of the present invention. FIG. 5 (a) shows a perspective view, FIG. 5 (b) shows a plan view, FIG. 5 (c) shows a side view, and FIG. 5 (d) shows an illustration. FIG. 6 is an illustration showing propagation behavior of an ultrasonic wave in the ultrasonic testing equipment shown in FIG. 5. FIG. 6 (a) shows a perspective view, FIG. 6 (b) shows a sectional view in a circumferential direction of a pipe, FIG. 6 (c) shows a plan view, and FIG. 6 (d) shows a sectional view along a propagation plane (plane containing points O, A, and B shown in FIG. 6 (b)) of ultrasonic waves. As shown in FIG. 5, an ultrasonic testing equipment 100A according to the present embodiment is, like the ultrasonic testing equipment 100 according to the first embodiment, an ultrasonic testing equipment for detecting a flaw in the pipe P having an ultrasonic probe 1A and a transmission/reception control means 2A for controlling transmission/reception of an ultrasonic wave by the ultrasonic probe 1A. Also, the ultrasonic testing equipment 100A according to the present embodiment has, like the ultrasonic testing equipment 100 according to the first embodiment, the flaw decision circuit 3 for detecting flaws existing in the pipe P by comparing an amplitude of an echo from the pipe P with a predetermined threshold and the alarm—etc. output means 4 for outputting a predetermined warning or the like when a flaw is detected by the flaw decision circuit 3. Since the configuration of apparatuses of a transmission/reception control means 2A is the same as that of the transmission/reception control means 2 of the ultrasonic testing equipment 100 according to the first embodiment, a detailed description thereof is omitted.

The ultrasonic probe 1A has a plurality of transducers 11 arranged along an annular curved surface, and the annular curved surface is a curved surface obtained by cutting a predetermined spheroid M with two parallel planes S1 and S2 facing to each other that do not pass through a center O of the spheroid M and do not sandwich the center O of the spheroid M, said two parallel planes S1 and S2 being orthogonal to the rotational axis of the spheroid M (See FIG. 5 (c) and FIG. 5 (d)). Then, the ultrasonic probe 1A is arranged so as to face the pipe P so that a longer axis direction (x direction shown in FIG. 5 (b)) thereof is along the axial direction of the pipe P, a shorter axis direction (y direction shown in FIG. 5 (b)) thereof is along the circumferential direction of the pipe P, and the center O of the spheroid M correctly faces an axial center of the pipe P.

The transmission/reception control means 2A operates to cause, among a plurality of transducers 11, at least two or more transducers 11 to transmit an ultrasonic wave to and receive an ultrasonic wave from the pipe P.

A concrete method of determining a shape (shape of an annular curved surface) of the ultrasonic probe 1A will be described below with reference to FIG. 6. The ultrasonic probe 1A, as shown in FIG. 6, is determined in a shape so that the center O of the spheroid M is located in the vicinity of the external surface of the pipe P (thus, an ultrasonic wave transmitted by each transducer 11 enters the pipe P through the center O as an incident point).

As shown in FIG. 6, an ultrasonic wave transmitted by each transducer 11 constituting the ultrasonic probe 1A enters the pipe P through point O (the center O of the spheroid) on an external surface of the pipe P and is reflected at point A on an internal surface of the pipe P before reaching point B on the external surface of the pipe P. Then, assume that an angle (propagation angle) formed by the propagation direction of the ultrasonic wave that entered the pipe P through point O (propagation direction viewed from the normal direction of a tangential plane of the pipe P including the incident point O) and a circumferential tangent L of the pipe P passing through the incident point O is γ (hereinafter called also as "propagation direction γ"), an external refraction angle (angle formed by a normal L1 at point B of the pipe P and an ultrasonic wave beam U in a propagation plane of ultrasonic waves shown in FIG. 6 (d)) at point B is θr, and an internal refraction angle (angle formed by a normal L2 at point A of the pipe P and the ultrasonic wave beam U in the propagation plane of ultrasonic waves shown in FIG. 6 (d)) at point A is θk. Also assume that an angle of incidence (angle formed by a normal L3 at the incident point O of the pipe P and the ultrasonic wave beam U before entering the pipe P in the propagation plane of ultrasonic waves shown in FIG. 6 (d)) of an ultrasonic wave into the pipe P is θw and an angle of refraction (angle formed by the normal L3 at the incident point O of the pipe P and the ultrasonic wave beam U after entering the pipe P in the propagation plane of ultrasonic waves shown in FIG. 6 (d)) of an ultrasonic wave into the pipe P is θs.

An ultrasonic wave that enters the pipe P at the angle of incidence θw shows geometrical-optical propagation behavior. That is, an ultrasonic wave that entered the pipe P at the angle of incidence θ propagates into the pipe P at the angle of refraction θs determined by Snell's law. Then, as derived geometrically, the external refraction angle θr will be equal to the angle of refraction θs. That is, the following equation (7) applies.

$$\sin \theta r = Vs/Vi \cdot \sin \theta w \quad (7)$$

where, in the above equation (7), Vs means the propagation velocity of an ultrasonic wave propagating in the pipe P and Vi is the propagation velocity of an ultrasonic wave in a coupling medium filled between the ultrasonic probe A1 and the pipe P.

The internal refraction angle θk represented by the equation (2) described above, on the other hand, as derived from the above equation (7) and the equations (3) to (6) described above, is a function of the angle of incidence θw, the propagation angle γ, and the ratio of thickness to outer diameter t/D of the pipe P. Then, the internal refraction angle θk is minimum and equal to the external refraction angle θr (=angle of refraction θs) when the propagation direction γ of an ultrasonic wave agrees with the axial direction of the pipe P (that is, the propagation angle γ=90°), and is maximum when the propagation direction γ of an ultrasonic wave agrees with the circumferential direction of the pipe P (that is, the propagation angle γ=0°), which is represented by the following equation (8).

$$\theta k = \sin^{-1} \frac{\sin \theta r}{1 - 2(t/D)} \quad (8)$$

Here, if the ratio of thickness to outer diameter t/D of the pipe P is several %, a difference between the internal refraction angle θk and external refraction angle θr calculated according to the above equation (8) is within about 10°. Therefore, a difference between the internal refraction angle θk when detecting internal surface flaws extending in the axial direction of the pipe P (detected by an ultrasonic wave whose propagation direction γ agrees with the circumferential direction of the pipe P) and the internal refraction angle θk (=θs) when detecting internal surface flaws extending in the circumferential direction of the pipe P (detected by an ultrasonic wave whose propagation direction γ agrees with the axial direction of the pipe P) falls within about 10° and thus no significant difference arises between both methods in detectability of internal surface flaws. However, if t/D of the pipe P is 15% or more, the internal refraction angle θk calculated according to the above equation (8) becomes larger than the external refraction angle θr by 20° or more (that is, by changing the propagation direction γ from the axial direction to the circumferential direction of the pipe P, the internal refraction angle θk becomes larger by 20° or more), significantly reducing detectability of internal surface flaws extending in the axial direction of the pipe P. Similarly, detectability of internal surface flaws with tilt angles between the axial direction and circumferential direction of the pipe P will also decrease as the internal refraction angle θ increases.

To control reduced detectability of flaws involved in changes of the internal refraction angle θk described above, the angle of refraction θs corresponding to each propagation direction γ can be changed (that is, the angle of incidence θw can be changed) so that, in accordance with the propagation direction γ of an ultrasonic wave (that is, in accordance with the tilt angle of flaws orthogonal to the propagation direction γ of an ultrasonic wave), the internal refraction angle θk corresponding to each propagation direction γ remains approximately constant.

Thus, the ultrasonic probe 1A according to the present embodiment is designed into a shape to allow the angle of incidence θw corresponding to each propagation direction γ to change in accordance with the propagation direction γ of an ultrasonic wave transmitted by each transducer 11 so that the internal refraction angle θk corresponding to each propagation direction γ remains approximately constant. As described above, the ultrasonic probe 1A has a plurality of transducers 11 arranged along an annular curved surface, and the annular curved surface is a curved surface obtained by cutting the predetermined spheroid M with two parallel planes S1 and S2 facing to each other that do not pass through the center O of the spheroid M and do not sandwich the center O of the spheroid M, said two parallel planes S1 and S2 being orthogonal to the rotational axis of the spheroid M (See FIG. 5 (c) and FIG. 5 (d)). Thus, the propagation direction γ of an ultrasonic wave transmitted by each transducer 11 is within the range of −180° to 180°. The elevation angle of each transducer 11 viewed from the center O of the spheroid M is different depending on the position where each transducer 11 is arranged. In other words, the elevation angle of each transducer 11 is determined in accordance with the longer and shorter axes of the ultrasonic probe 1A and the distance from the center O of the spheroid M of the ultrasonic probe 1A, and the elevation angle is different depending on the position where each transducer 11 is arranged (depending on the propagation direction γ of an ultrasonic wave transmitted by each transducer 11). An angle obtained by subtracting the elevation angle from 90° corresponds to the angle of incidence θw. Therefore, the ultrasonic probe 1A according to the present embodiment is designed into a shape to allow the angle of incidence θw corresponding to each propagation direction γ to change in accordance with the propagation direction γ of an ultrasonic wave transmitted by each transducer 11 so that the internal refraction angle θk corresponding to each propagation direction γ remains approximately constant by setting the longer and shorter axes of the ultrasonic probe 1A and the distance from the center O of the spheroid M of the ultrasonic probe 1A appropriately.

More concretely, as shown in FIG. 5, if the longer axis of the ultrasonic probe 1A is 2x, the shorter axis is 2y, and the distance from the center O of the spheroid M (average distance from the center O of the spheroid M to the planes S1 and S2) is h, the angle of incidence θw (called θw1) of an ultrasonic wave transmitted by an transducer 11 located on the longer axis of the ultrasonic probe 1A and the angle of incidence θw (called θw2) of an ultrasonic wave transmitted by an transducer 11 located on the shorter axis of the ultrasonic probe 1A are given by the following equations (9) and (10) respectively.

$$\theta w1 = \tan^{-1}(x/h) \quad (9)$$

$$\theta w2 = \tan^{-1}(y/h) \quad (10)$$

The shape (x, y, and h) of the ultrasonic probe 1A is determined in accordance with t/D of the pipe P in which flaws should be detected so that the angles of incidence θw1 and θw2 represented by the above equations (9) and (10) satisfy a the following equation (11).

$$\sin \theta w2 = \sin \theta w1 \cdot \{1 - 2(t/D)\} \quad (11)$$

With the angles of incidence θw1 and θw2 satisfying the above equation (11), the internal refraction angle θk when the propagation direction γ of an ultrasonic wave agrees with the axial direction of the pipe P (when an ultrasonic wave is transmitted from an transducer 11 located on the longer axis of the ultrasonic probe 1A) and the internal refraction angle θk when the propagation direction γ of an ultrasonic wave agrees with the circumferential direction of the pipe P (when an ultrasonic wave is transmitted from a transducer 11 located on the shorter axis of the ultrasonic probe 1A) are approximately equal. This makes it possible to obtain an approximately equal internal refraction angle θk also when the propagation direction γ of an ultrasonic wave is between the axial direction and circumferential direction of the pipe P. That is, an approximately equal internal refraction angle θk will be obtained when the propagation direction γ of an ultrasonic wave is any in the range of −180° to 180°.

The reason why the internal refraction angle θk (called θk1 below when deemed appropriate) of an ultrasonic wave transmitted by an transducer 11 located on the longer axis of the ultrasonic probe 1A and the internal refraction angle θk (called θk2 below when deemed appropriate) of an ultrasonic wave transmitted by an transducer 11 located on the shorter axis of the ultrasonic probe 1A are approximately equal when the angles of incidence θw1 and θw2 satisfy the above equation (11) is as follows. That is, if the angle of refraction of an ultrasonic wave transmitted by an transducer 11 located on the longer axis of the ultrasonic probe 1A is θs1 and the angle of refraction of an ultrasonic wave transmitted by an transducer 11 located on the shorter axis of the ultrasonic probe 1A is θs2, these angles of refraction are given according to Snell's law by the following equations (12) and (13) respectively.

$$\sin\theta s1 = Vs/Vi \cdot \sin\theta w1 \tag{12}$$

$$\sin\theta s2 = Vs/Vi \cdot \sin\theta w2 \tag{13}$$

where, in the above equations (12) and (13), Vs means the propagation velocity of an ultrasonic wave (ultrasonic shear wave) propagating in the pipe P and Vi is the propagation velocity of an ultrasonic wave (ultrasonic longitudinal wave) in a coupling medium filled between the transducer 11 and the pipe P.

Since an ultrasonic wave transmitted by an transducer 11 located on the longer axis of the ultrasonic probe 1A is propagated in the axial direction of the pipe P, a relation in the following equation (14) holds between the internal refraction angle θk1 and the angle of refraction θs1, like as described above with reference to FIG. 6. On the other hand, since an ultrasonic wave transmitted by an transducer 11 located on the shorter axis of the ultrasonic probe 1A is propagated in the circumferential direction of the pipe P, a relation in the following equation (15) holds between the internal refraction angle θk2 and the angle of refraction θs2, like the equation (8) as described above.

$$\theta k1 = \theta s1 \tag{14}$$

$$\sin\theta k2 = \sin\theta s2/\{1-2(t/D)\} \tag{15}$$

If, here, θk1=θk2, sin θk1=sin θk2 holds. Applying the above equations (15) and (13) to sin θk2 yields a relation in the following equation (16).

$$\begin{aligned}\sin\theta k1 &= \sin\theta k2 \\ &= \sin\theta s2/\{1-2(t/D)\} \\ &= Vs/Vi \cdot \sin\theta w2/\{1-2(t/D)\}\end{aligned} \tag{16}$$

Applying the above equations (14) and (12) to sin θk1, on the other hand, yields a relation in the following equation (17).

$$\begin{aligned}\sin\theta k1 &= \sin\theta s1 \\ &= Vs/Vi \cdot \sin\theta w1\end{aligned} \tag{17}$$

Therefore, from the above equations (16) and (17), a relation in the following equation (18) holds, which yields the above equation (11) after some calculation. That is, the above equation (11) holds when θk1=θk2.

$$Vs/Vi \cdot \sin\theta w2/\{1-2(t/D)\} = Vs/Vi \cdot \sin\theta w1 \tag{18}$$

As described above, the above equation (11) holds when θk1=θk2 and conversely, when the above equation (11) is satisfied, θk1=θk2 holds. In other words, if the angles of incidence θw1 and θw2 satisfy the above equation (11), the internal refraction angle θk (θk1) of an ultrasonic wave transmitted by an transducer 11 located on the longer axis of the ultrasonic probe 1A and the internal refraction angle θk (θk2) of an ultrasonic wave transmitted by an transducer 11 located on the shorter axis of the ultrasonic probe 1A will be approximately equal.

Since the shape of the ultrasonic probe 1A according to the present embodiment has been determined as described above, it is possible to cause the propagation direction γ of an ultrasonic wave transmitted by each transducer 11 and the extension direction of flaws to be detected to are orthogonal to each other and, at the same time, to maintain the internal refraction angle θk approximately constant so that equivalent echo intensity can be obtained regardless of the tilt angle of each flaw. By selecting as many transducers 11 as the number of tilt angles of flaws to be detected by the transmission/reception control means 2A and causing each selected transducer 11 to transmit and receive an ultrasonic wave, as described above, flaws with various tilt angles can be detected with high precision.

Many combinations of the angles of incidence θw1 and θw2 (that is, combinations of x, y, and h) satisfying the above equation (11) exist, but like a general angle beam method, to reduce ultrasonic longitudinal waves entering the pipe P even in small amounts, the shape (x, y, and h) of the ultrasonic probe 1A can be determined so that at least ultrasonic waves transmitted by transducers 11 (transducers from which an ultrasonic wave is transmitted with the largest angle of incidence θw into the pipe and, as a result, the largest angle of refraction θs) located on the longer axis of the ultrasonic probe 1A propagate into the pipe P with the angle of refraction of shear wave θs of 35° or more. In this case, in consideration of not only the ratio of thickness to outer diameter (t/D) described above, but also the propagation velocity of an ultrasonic wave propagating in the pipe P and the propagation velocity of an ultrasonic wave in a coupling medium filled between the ultrasonic probe 1A and the pipe P, from among combinations of x, y, and h satisfying the above equation (11), such combinations should be selected that at least ultrasonic waves transmitted by transducers 11 located on the longer axis of the ultrasonic probe 1A propagate into the pipe P with the angle of refraction of shear wave θs of 35° or more.

That is, when the ultrasonic probe 1A is arranged so as to face the pipe P so that the longer axis direction of the ultrasonic probe 1A is along the axial direction of the pipe P, the shorter axis direction of the ultrasonic probe 1A is along the circumferential direction of the pipe P, and the center O of the spheroid correctly faces the axial center of the pipe P, the longer axis 2x and shorter axis 2y of the ultrasonic probe 1A and the distance h from the center O of the spheroid of the ultrasonic probe 1A are preferably set based on the ratio of thickness to outer diameter (t/D) of the pipe P, the propagation velocity of an ultrasonic wave propagating in the pipe P, and the propagation velocity of an ultrasonic wave in a coupling medium filled between the ultrasonic probe 1A and the pipe P so that at least ultrasonic waves transmitted, among a plurality of transducers 11, by transducers 11 located on the longer axis of the ultrasonic probe 1A propagate into the pipe P with the angle of refraction of shear wave θs of 35° or more.

According to the ultrasonic probe 1A having a preferable shape determined as described above, at least ultrasonic waves transmitted by transducers 11 located on the longer axis of the ultrasonic probe 1A (that is, ultrasonic waves propagating in the axial direction of the pipe P) can be caused to propagate as ultrasonic shear waves in the pipe P.

The ultrasonic probe 1A according to the present embodiment is preferably arranged so that the center O of the spheroid is located in the vicinity of the external surface of the pipe P not only when determining the shape, but also when actually detecting flaws.

Since, according to such a preferable apparatus, the incident point of an ultrasonic wave transmitted by each transducer 11 into the pipe P will approximately agree (The center O of the spheroid will be an incident point), propagation behavior of an ultrasonic wave planned when determining the shape of the ultrasonic probe 1A can be obtained (The internal refraction angle θk is approximately constant regardless of the propagation direction of an ultrasonic wave) and, as a result, flaws with various tilt angles can be detected with high precision.

The transmission/reception control means 2A of the ultrasonic testing equipment 100A according to the present embodiment, like the transmission/reception control means 2 according to the first embodiment controls, preferably, transmission time-shift or reception time-shift of ultrasonic waves of the one transducer 11 and the another transducer 11 so that, among at least two or more transducers 11 that transmit an ultrasonic wave to and receive an ultrasonic wave from the pipe P, a surface echo on the pipe P of an ultrasonic wave transmitted by the one transducer and another surface echo on the pipe P of an ultrasonic wave transmitted by the another transducer are received at approximately the same time (so that a time difference is equal to or less than a pulse width of a transmitted ultrasonic wave, for example).

Since, according to such a preferable apparatus, a surface echo on the pipe P of an ultrasonic wave transmitted by the one transducer and another surface echo on the pipe P of an ultrasonic wave transmitted by the another transducer are received at approximately the same time, even if an echo received by each transducer 11 is synthesized by a waveform synthesis circuit (not shown), like the first embodiment, a circumstance, in which a width of echoes is broadened because surface echoes on the pipe P surfaces (internal and external surfaces) received by each transducer 11 are continuous or partly overlapped, can hardly occur, and thus a dead zone in the vicinity of the internal and external surfaces of the pipe P can be reduced.

As described above, the shape (x, y, and h) of the ultrasonic probe 1A according to the present invention is determined in accordance with t/D of the pipe P in which flaws should be detected and the like. In other words, an appropriate shape of the ultrasonic probe 1A changes depending on t/D of the pipe P in which flaws should be detected and the like. Therefore, there is a problem in cost and maintenance because ultrasonic probes 1A of appropriate shapes must be prepared individually for pipes with various sizes of t/D and the like.

To solve such a problem, an adjustment means for adjusting the angle of incidence θw of an ultrasonic wave transmitted by each of a plurality of transducers 11 to the pipe P should preferably be provided. Since this makes it possible to fine-tune the angle of incidence θw of an ultrasonic wave transmitted by each of a plurality of transducers 11 to the pipe P so that the propagation direction γ of an ultrasonic wave transmitted from each transducer 11 and the extension direction of flaws to be detected can be made to are orthogonal to each other, while at the same time, the internal refraction angle θk can be maintained approximately constant (as the equation (11) is satisfied) even if the ultrasonic probes 1A have the same shape (x, y, and h), there is no need for preparing ultrasonic probes 1A with various shapes in accordance with t/D of the pipe P, and thus an advantage in cost and maintainability is gained.

As the adjustment means, for example, a mechanical declination mechanism can be adopted. In addition, as shown in FIG. 5 (a), each of the plurality of transducers 11 has a plurality of piezoelectric elements 111 divided into a rectangular shape along a radial direction of each transducer 11, and the adjustment means (for example, the transmission/reception control means 2A functions as the adjustment means) can also adjust the angle of incidence θw of an ultrasonic wave transmitted to the pipe P by electrically controlling transmission/reception time-shift of an ultrasonic wave by the plurality of piezoelectric elements 111. In this case, compared with a case of adopting a mechanical declination mechanism, the angle of incidence θw can be adjusted more easily with improved reproducibility.

According to the shape of the ultrasonic probe 1A in the present invention, the internal refraction angle θk can be maintained approximately constant while the external refraction angle θr changes depending on the propagation direction γ. In other words, the ultrasonic probe 1A according to the present invention has a shape suitable in use for detecting internal surface flaws with various tilt angles with high precision. In contrast, to detect external surface flaws with various tilt angles with high precision, the external refraction angle θr must be maintained approximately constant regardless of the tilt angle of each flaw (that is, regardless of the propagation direction γ of an ultrasonic wave). Since the external refraction angle θr is equal to the angle of refraction θs, as described above, the angle of refraction θs may be maintained approximately constant regardless of the propagation direction γ and, for this purpose, the angle of incidence θw may be maintained approximately constant regardless of the propagation direction γ. To maintain the angle of incidence θw approximately constant regardless of the propagation direction γ of an ultrasonic wave, the longer axis (2x) and the shorter axis (2y) of the ultrasonic probe may be set to approximately equal values. That is, a shape obtained when the spheroid is assumed to be a sphere may be set. According to the ultrasonic probe in such a shape, the external refraction angle θr can be made to be approximately constant regardless of the propagation direction γ and external surface flaws with various tilt angles can be detected with high precision.

Then, depending on whether main flaws in the pipe P to be detected are internal surface flaws or external surface flaws, the shape of the ultrasonic probe suitable for detecting each type of flaw may be selected. Or, if both internal and external surface flaws should be detected simultaneously, a shape having approximately intermediate x and y values of a shape (x, y, and h) of the ultrasonic probe satisfying the equation (11) suitable for detecting internal surface flaws and a shape of the ultrasonic probe satisfying x=y suitable for detecting external surface flaws may be adopted.

By showing examples and comparative examples below, features of the present invention will be made more evident.

Example 1 (See FIG. 3)

Using the ultrasonic testing equipment 100 whose outline configuration is shown in FIG. 3, an ultrasonic testing of a plurality of internal surface flaws (depth 0.5 mm×length 25.4 mm) with mutually different tilt angles (tilt angles of 0°, 10°, 20°, 30°, and 45°) formed on the internal surface of a steel pipe was carried out. Here, the ultrasonic probe 1 has a plurality (30) of transducers 11 of length 5 mm×width 3 mm with oscillating frequency 2 MHz arranged on a cylinder curved with a radius of curvature of 200 mm in a matrix state (10 rows×3 columns) in the row direction (axial direction of the steel pipe). When deemed appropriate below, transducers 11 arranged in the first column are called #1 to #10, transducers 11 arranged in the second column are called #11 to #20, and transducers 11 arranged in the third column are called #21 to #30.

Table 1 shows the axial angle of incidence $\beta i$, the propagation direction $\gamma$, and the internal refraction angle $\theta k$ of an ultrasonic wave transmitted by the transducer #1 and another transducers #2 to #30 when the eccentricity of the ultrasonic probe 1 is adjusted (that is, the circumferential angle of incidence $\alpha i$ of the transducer #1 is adjusted) so that the transducer #1 in the first column is optimal for detection of internal surface flaws with the tilt angle 0°.

TABLE 1

| transducer # | $\beta i$ (°) | $\gamma$ (°) | $\theta k$ (°) |
|---|---|---|---|
| Group of transducers in the first column | | | |
| 1 | 0 | 0 | 40 |
| 2 | 1 | 5 | 41 |
| 3 | 2 | 9 | 41 |
| 4 | 4 | 14 | 42 |
| 5 | 5 | 18 | 42 |
| 6 | 6 | 22 | 43 |
| 7 | 7 | 26 | 44 |
| 8 | 9 | 30 | 46 |
| 9 | 10 | 33 | 48 |
| 10 | 11 | 36 | 49 |
| Group of transducers in the second column | | | |
| 11 | 0 | 0 | 35 |
| 12 | 1 | 5 | 35 |
| 13 | 2 | 10 | 36 |
| 14 | 4 | 15 | 36 |
| 15 | 5 | 20 | 37 |
| 16 | 6 | 25 | 38 |
| 17 | 7 | 29 | 39 |
| 18 | 9 | 33 | 41 |
| 19 | 10 | 36 | 42 |
| 20 | 11 | 40 | 44 |
| Group of transducers in the third column | | | |
| 21 | 0 | 0 | 30 |
| 22 | 1 | 6 | 30 |
| 23 | 2 | 12 | 31 |
| 24 | 4 | 17 | 31 |
| 25 | 5 | 23 | 32 |
| 26 | 6 | 28 | 33 |
| 27 | 7 | 32 | 35 |
| 28 | 9 | 36 | 36 |
| 29 | 10 | 40 | 38 |
| 30 | 11 | 44 | 40 |

Here, the above-described method described in Patent Literature 2 is a method by which the axial angle of incidence $\beta i$ is changed (on condition that the circumferential angle of incidence $\alpha i$ is maintained constant) to change the propagation direction $\gamma$ using, as it were, the transducers #1 to #10 in the first column, or the transducers #11 to #20 in the second column, or the transducers #21 to #30 in the third column only. However, as is evident from Table 1, using only transducers in the same column to change the propagation direction $\gamma$ also changes the internal refraction angle $\theta k$, and this changes detectability of flaws.

In contrast, in the ultrasonic testing equipment 100 in the present example, the transmission/reception control means 2 operates to select, from among a plurality of transducers arranged in a matrix state, a group of transducers (transducers #1 and #3 in the present example) including at least one transducer 11 arranged in the first column and to cause the selected group of transducers to transmit and receive an ultrasonic wave in one propagation direction in the steel pipe. Also, the control circuit 23 selects, from among a plurality of transducers arranged in a matrix state, another group of transducers (in the present example, a group of transducers composed of the transducers #15 and #17 in the second column and another group of transducers composed of the transducer #30 in the third column) including at least one transducer whose position in the row and column directions is different from that of any transducer constituting the above group of transducers, and to cause the selected groups of transducers to transmit and receive an ultrasonic wave in other propagation directions in the steel pipe.

More concretely, the transmission/reception control means 2 in the present example operates to, (1) select the transducer #1 in the first column to detect internal surface flaws with the tilt angle 0°, (2) select the transducer #3 in the first column to detect internal surface flaws with the tilt angle 10°, (3) select the transducer #15 in the second column to detect internal surface flaws with the tilt angle 20°, (4) select the transducer #17 in the second column to detect internal surface flaws with the tilt angle 30°, (5) select the transducer #30 in the third column to detect internal surface flaws with the tilt angle 45°, and to cause the selected transducers #1, #3, #15, #17, and #30 to approximately simultaneously to transmit and receive ultrasonic waves.

As is evident from Table 1, this makes it possible to cause each internal surface flaw with a mutually different tilt angle and the propagation direction $\gamma$ of an ultrasonic wave to are orthogonal to each other (to make the $\gamma$ value and the tilt angle of internal surface flaws to be detected approximately equal) and at the same time, to make the internal refraction angle $\theta k$ take an approximately constant value (about 40°).

Figure 7:
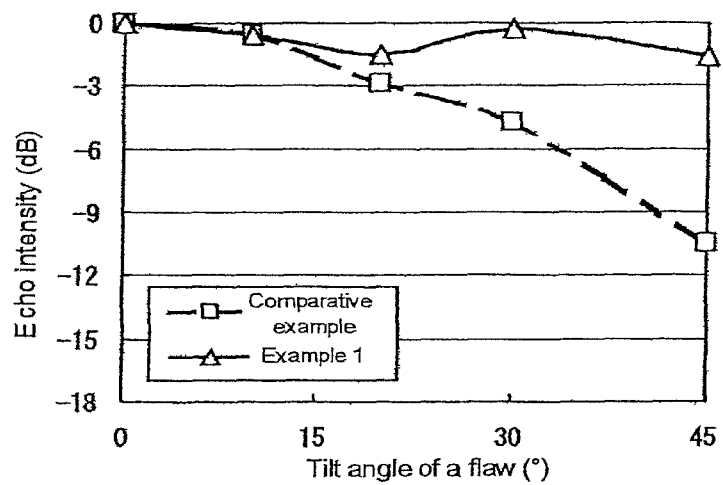
FIG. 7 shows echo intensity by each internal surface flaw obtained by carrying out an ultrasonic testing using an ultrasonic testing equipment according to the first example of the present invention.

FIG. 7 shows echo intensity (relative intensity when the echo intensity by an internal surface flaw with the tilt angle 0° is defined to be 0 dB) by each internal surface flaw obtained by carrying out an ultrasonic testing using the ultrasonic testing equipment 100 according to the present example. FIG. 7 also shows, as a comparative example, echo intensity by each internal surface flaw obtained when each internal surface flaw and the propagation direction $\gamma$ of an ultrasonic wave are made to are orthogonal to each other by changing only the axial angle of incidence $\beta i$ on condition that the circumferential angle of incidence $\alpha i$ is maintained constant (that is, by using only transducers 11 arranged in the same column). As shown in FIG. 7, the present experiment shows that, while echo intensity decreases as the tilt angle of a flaw increases in the comparative example and, as a result, reduced detectability of flaws is caused, approximately equivalent echo intensity is obtained for internal surface flaws in the tilt angle of 0° to 45° in the present example and, as a result, approximately constant detectability of flaws is obtained.

To reduce manufacturing costs by simplifying the circuit configuration, in the ultrasonic testing equipment 100 according to the present example, an echo received by each transducer 11 (transducer #1, #3, #15, #17, and #30) is synthesized by the waveform synthesis circuit 223 and, based on the synthesized echo, flaws are detected by the flaw decision circuit 3. Then, the transmission/reception control means 2 controls transmission time-shift or reception time-shift of an echo of each transducer 11 (A delay time of the corresponding delay circuit 212 or the delay circuit 222 is set) so that each surface echo on the steel pipe of an ultrasonic wave transmitted by each transducer 11 is received at approximately the same time (so that a time difference is equal to or less than a pulse width of a transmitted ultrasonic wave).

Figure 8:
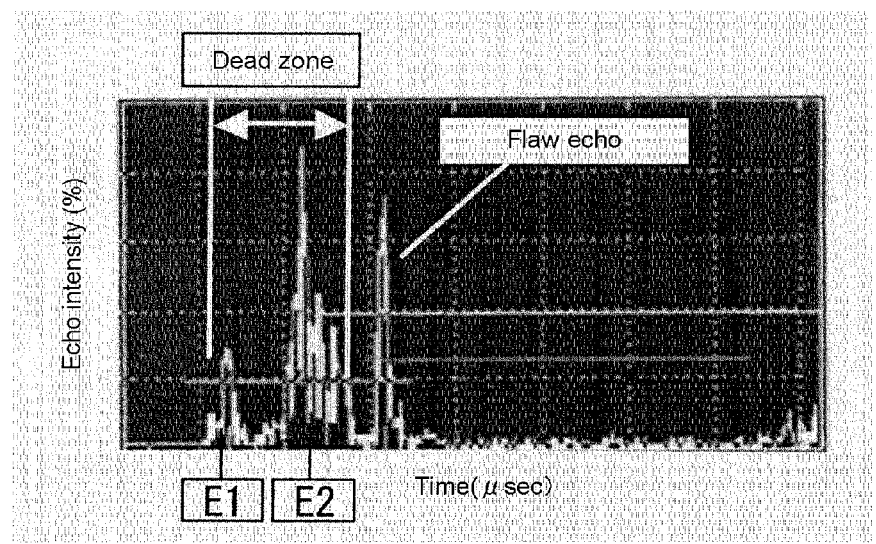
FIG. 8 shows an example of waveforms obtained when transmission time-shift or reception time-shift of an ultrasonic wave of each transducer is not controlled in the first example of the present invention.

FIG. 8 shows an example of waveforms obtained by synthesizing an echo each received by the transducers #1 and #30 (an echo steel pipe surface (external surface) each received by the transducers #1 and #30 and an echo (flaw echo) from internal surface flaws with the tilt angle 45° detected by the transducer #30) using the waveform synthesis circuit 223 when ultrasonic waves are approximately simultaneously transmitted by the transducers #1 and #30 without controlling transmission time-shift or reception time-shift of the ultrasonic waves of the transducers #1 and #30. In FIG. 8, a waveform E1 corresponds to an echo on the steel pipe surface received by the transducer #30 and a waveform E2 corresponds to an echo on the steel pipe surface received by the transducer #1. As shown in FIG. 8, without controlling transmission time-shift or reception time-shift of ultrasonic waves of the transducers #1 and #30, the waveform E1 and waveform E2 are continuous or partly overlapped, leading to a broadened width of overall echoes on the steel pipe surface to increase a dead zone in the vicinity of steel pipe external surface. This is a phenomenon caused by a difference between a beam path length of an ultrasonic wave transmitted by the transducer #1 before reaching the steel pipe external surface and that of an ultrasonic wave transmitted by the transducer #30 before reaching the steel pipe external surface.

Figure 9:
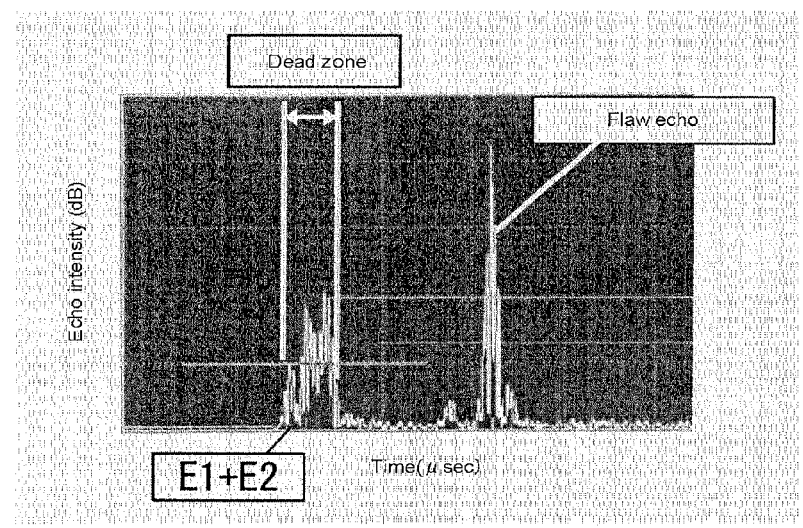
FIG. 9 shows an example of waveforms obtained when transmission time-shift of an ultrasonic wave of each transducer is controlled in the first example of the present invention.

In contrast, since the transmission/reception control means 2 according to the present example, as described above, controls transmission time-shift or reception time-shift of an ultrasonic wave from each transducer 11 so that each surface echo on the steel pipe of an ultrasonic wave transmitted by each transducer 11 is received at approximately the same time, a dead zone can be reduced compared with the case shown in FIG. 8. FIG. 9 shows an example of waveforms obtained by synthesizing an echo each received by the transducers #1 and #30 using the waveform synthesis circuit 223 after delaying transmission timing of the transducer #30 by a predetermined time with respect to the transducer #1 using the transmission/reception control means 2 according to the present example. As shown in FIG. 9, by delaying transmission timing of the transducer #30 by a predetermined time with respect to the transducer #1 using the transmission/reception control means 2 according to the present example, the waveform E1 and waveform E2 are approximately completely overlapped. Though the width of synthetic waveforms (E1+E2) of the waveforms E1 and E2 shown in FIG. 9 is a little broader than that of the waveforms E1 shown in FIG. 8, it is found that the dead zone can be reduced to about ⅓ or less compared with the dead zone shown in FIG. 8.

Example 2 (See FIG. 5)

Using the ultrasonic testing equipment 100A whose outline configuration is shown in FIG. 5, an ultrasonic testing of a plurality of internal surface flaws (depth 0.5 mm×length 25.4 mm) with mutually different tilt angles formed on the internal surface of a steel pipe (t/D=11%) was carried out. Here, the ultrasonic probe 1A has a plurality (32) of transducers 11 of length 5 mm×width 3 mm with oscillating frequency 2 MHz arranged along an annular curved surface obtained by cutting a predetermined spheroid with two parallel planes S1 and S2 facing to each other that do not pass through a center O of the spheroid and do not sandwich the center O of the spheroid, said two parallel planes S1 and S2 being orthogonal to the rotational axis of the spheroid. The shape of the ultrasonic probe 1A was determined so that the angle of incidence $\theta w1$ represented by the above-described equation (9) is about 18° and the angle of incidence $\theta w2$ represented by the equation (10) is about 14°. Such angles of incidence $\theta w1$ and $\theta w2$ satisfy the above-described equation (11).

Then, an ultrasonic testing was carried out in a state where the ultrasonic probe 1A is arranged so as to face the steel pipe so that the longer axis direction of the ultrasonic probe 1A is along the axial direction of the steel pipe, the shorter axis direction of the ultrasonic probe 1A is along the circumferential direction of the steel pipe, and the center O of the spheroid correctly faces the axial center of the steel pipe to be located in the vicinity of the external surface of the steel pipe. Water was used as a coupling medium to be filled between the ultrasonic probe 1A and the steel pipe.

Here, since the propagation velocity of an ultrasonic wave (ultrasonic shear wave) in the steel pipe is 3200 m/sec and the propagation velocity of an ultrasonic wave (ultrasonic longitudinal wave) in water, which is a coupling medium, is 1500 m/sec, the angle of refraction (angle of refraction corresponding to the angle of incidence $\theta w1$) $\theta s$ (called $\theta s1$) of an ultrasonic wave transmitted by transducers 11 located on the longer axis of the ultrasonic probe 1A becomes about 41° and the angle of refraction (angle of refraction corresponding to the angle of incidence $\theta w2$) $\theta s$ (called $\theta s2$) of an ultrasonic wave transmitted by transducers 11 located on the shorter axis of the ultrasonic probe 1A becomes about 31°.

As described above, the external refraction angle $\theta r$ of an ultrasonic wave becomes equal to the angles of refraction $\theta s1$ and $\theta s2$, and the internal refraction angle $\theta k$ of an ultrasonic wave is represented as a function of the angle of incidence $\theta w$, propagation direction $\gamma$, and t/D of the pipe P. That is, the internal refraction angle $\theta k$ takes a minimum value and is equal to the angle of refraction $\theta s1$ when the propagation direction $\gamma$ agrees with the axial direction of the steel pipe. In other words, the internal refraction angle $\theta k$ becomes about 41°. The angle of refraction $\theta s$ generally increases as the propagation direction $\gamma$ deflects from the axial direction of the steel pipe to the circumferential direction and the internal refraction angle $\theta k$ takes a maximum value, which is represented by the above-described equation (8), when the propagation direction $\gamma$ agrees with the circumferential direction of the steel pipe. In the present example, the internal refraction angle $\theta k$ is obtained by substituting t/D=11% and $\theta s$ ($\theta s2$) =31° into the equation (8), yielding about 41°, which is an equivalent value of the internal refraction angle $\theta k$ when the propagation direction $\gamma$ agrees with the axial direction of the steel pipe. Thus, an approximately equivalent internal refraction angle $\theta k$ is also obtained when the propagation direction $\gamma$ of an ultrasonic wave is between the axial direction and circumferential direction of the steel pipe. That is, an approximately equivalent internal refraction angle $\theta k$ will be obtained when the propagation direction $\gamma$ of an ultrasonic wave is any in the range of −180° to 180°.

Since the shape of the ultrasonic probe 1A according to the present example is determined as described above, it is possible to cause the propagation direction γ of an ultrasonic wave transmitted by each transducer 11 and the extension direction of flaws to be detected to are orthogonal to each other and, at the same time, to maintain the internal refraction angle θk approximately constant regardless of the tilt angle.

Figure 10:
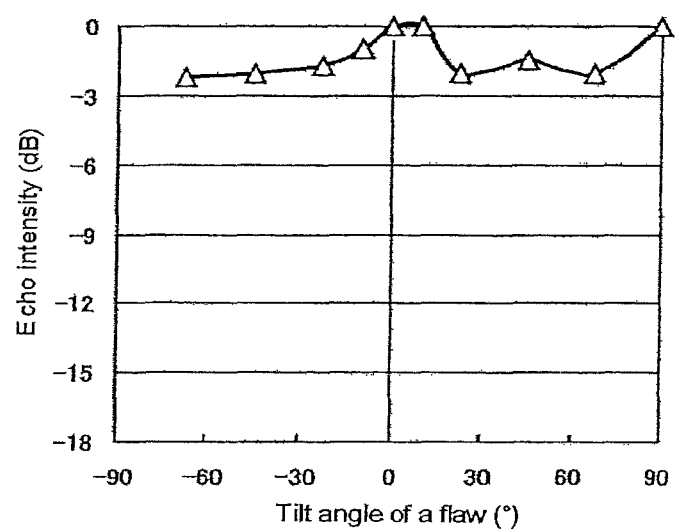
FIG. 10 shows echo intensity by each internal surface flaw obtained by carrying out an ultrasonic testing using an ultrasonic testing equipment according to the second example of the present invention.

FIG. 10 shows echo intensity (relative intensity when the echo intensity by an internal surface flaw with the tilt angle 0° is defined to be 0 dB) by each internal surface flaw obtained by carrying out an ultrasonic testing using the ultrasonic testing equipment 100A according to the present example. As shown in FIG. 10, it is found that approximately equivalent echo intensity is obtained using the ultrasonic testing equipment 100A according to the present example for internal surface flaws with the tilt angles of 67.5° to 90° and, as a result, approximately equivalent detectability of flaws is obtained.

By adopting, also for the ultrasonic testing equipment 100A according to the present example like the ultrasonic testing equipment 100 according to the first example, a configuration in which the transmission/reception control means 2A controls transmission time-shift or reception time-shift of an ultrasonic wave of each transducer 11 so that each surface echo on the steel pipe of an ultrasonic wave transmitted by each transducer 11 is received at approximately the same time, flaws with various tilt angles can quickly be detected and a dead zone in the vicinity of steel pipe surface can be reduced.

Third Example (See FIG. 5)

Using the ultrasonic testing equipment 100A whose outline configuration is shown in FIG. 5, an ultrasonic testing similar to that in the second example was carried out. However, the experiment conditions are different in which each of a plurality of transducers 11 incorporated in the ultrasonic probe 1A is composed of eight piezoelectric elements 111 divided into a rectangular shape along the radial direction of each transducer 11 and steel pipes whose t/D is 5% and 14%, as well as 11% were included as test object.

The shape of the ultrasonic probe 1A was determined, like the second example, to be optimal for a steel pipe with t/D=11% and the angle of incidence θw of an ultrasonic wave transmitted into the steel pipes was adjusted by electrically controlling transmission/reception time-shift of ultrasonic waves by a plurality of piezoelectric elements 111 using the transmission/reception control means 2A so that approximately equivalent detectability of flaws is obtained for steel pipes of other t/D.

Figure 11:
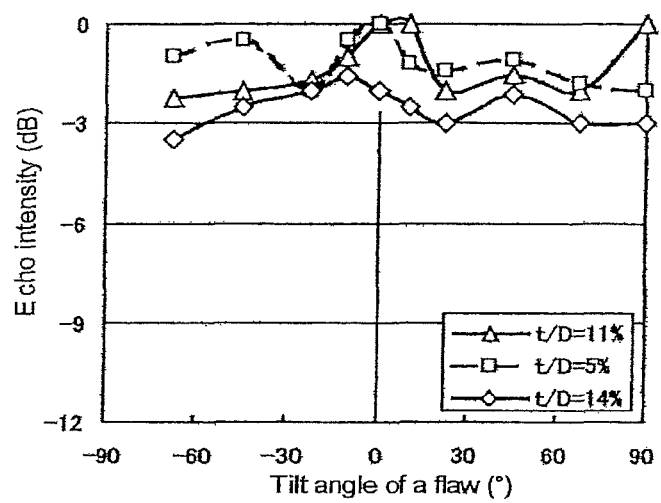
FIG. 11 shows echo intensity by each internal surface flaw formed on a steel pipe of each t/D by carrying out an ultrasonic testing using an ultrasonic testing equipment according to the third example of the present invention.

FIG. 11 shows echo intensity (relative intensity when the echo intensity by an internal surface flaw with the tilt angle 0° formed on a steel pipe of t/D=11% is defined to be 0 dB) by each internal surface flaw formed on a steel pipe of each t/D obtained by carrying out an ultrasonic testing using the ultrasonic testing equipment 100A. As shown in FIG. 11, it is found that approximately equivalent echo intensity is obtained using the ultrasonic testing equipment 100A according to the present example for internal surface flaws with the tilt angles of −70° to 90° in steel pipes whose t/D is 5% to 14% and, as a result, approximately equivalent detectability of flaws is obtained.

Fourth Example

Figure 12:
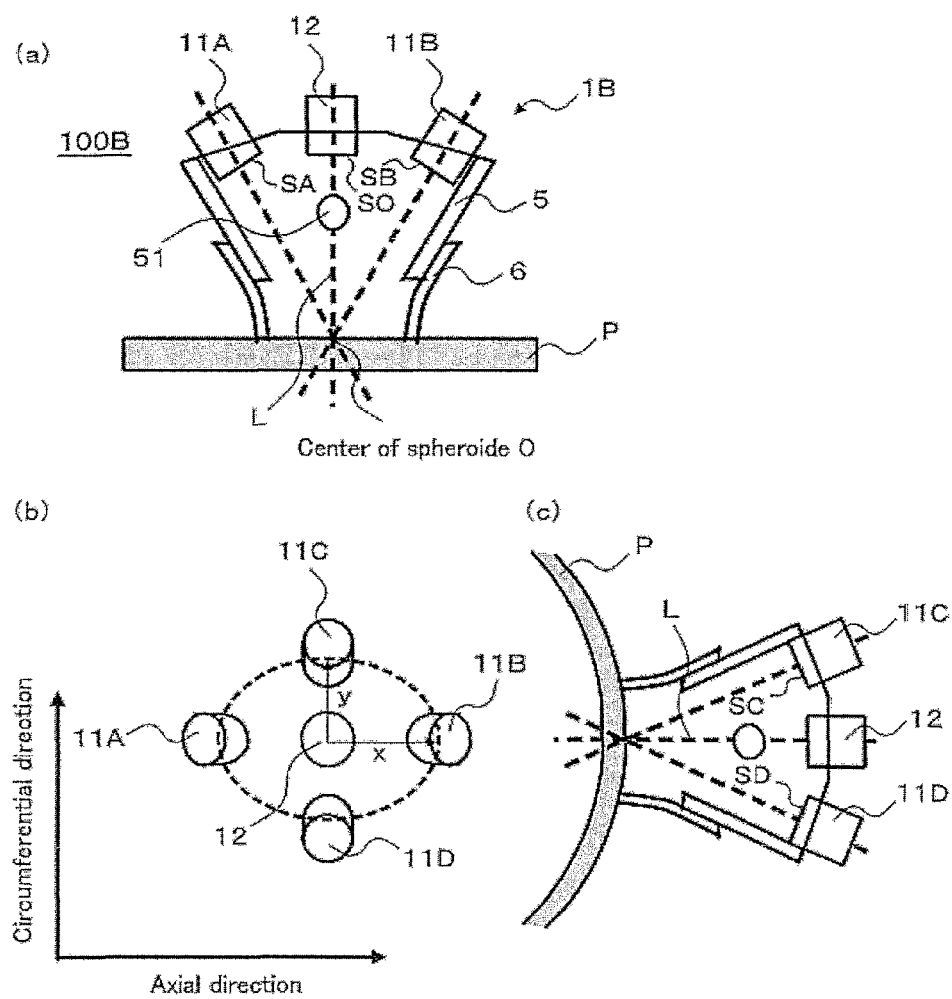
FIG. 12 is a diagram showing the outline configuration of an ultrasonic testing equipment according to the fourth example of the present invention.

The present example is a variant of the above-described second example and a flaws detection experiment of internal surface flaws formed on the internal surface of a steel pipe (t/D=11%) was carried out. FIG. 12 shows the outline configuration of an ultrasonic testing equipment 100B according to the present example. FIG. 12 (a) shows a front sectional view, FIG. 12 (b) shows a plan view, and FIG. 12 (c) shows a side sectional view. As shown in FIG. 12, the ultrasonic testing equipment 100B according to the present example has an ultrasonic probe 1B equipped with four transducers (angle beam probe) 11A, 11B, 11C, and 11D with oscillating frequency 5 MHz and a straight beam probe 12 with oscillating frequency 5 MHz, an acrylic cabinet 5 in which these transducers 11A to 11D and the straight beam probe 12 are mounted, and a soft hose 6 connected to a tip of the cabinet 5. The ultrasonic testing equipment 100B according to the present example has, like the second example, a transmission/reception control means (See the transmission/reception control means 2A shown in FIG. 5) for controlling transmission/reception of an ultrasonic wave by the ultrasonic probe 1B. The ultrasonic testing equipment 100B also has the flaw decision circuit 3 (See FIG. 5) for detecting flaws existing in a steel pipe P by comparing an amplitude of an echo from the steel pipe P with a predetermined threshold and the alarm-etc. output means 4 (See FIG. 5) for outputting a predetermined warning or the like when a flaw is detected by the flaw decision circuit 3. Since the configuration of apparatuses of a transmission/reception control means in the present example is the same as that of the transmission/reception control means 2 shown in FIG. 3, a detailed description thereof is omitted.

The four transducers 11A to 11D incorporated in the ultrasonic probe 1B are arranged, like the second example, so that transducer surfaces SA to SD are arranged along an annular curved surface obtained by cutting a predetermined spheroid with two parallel planes facing to each other that do not pass through the center O of the spheroid and do not sandwich the center O of the spheroid, said two parallel planes being orthogonal to the rotational axis of the spheroid. More concretely, the transducers 11A and 11B are arranged in the longer axis direction of the ultrasonic probe 1B (longer axis direction of the annular curved surface, which is the x direction shown in FIG. 12 (b)) so that the angle of incidence θw1 represented by the above-described equation (9) becomes about 18°. The transducers 11C and 11D are arranged in the shorter axis direction of the ultrasonic probe 1B (shorter axis direction of the annular curved surface, which is the y direction shown in FIG. 12 (b)) so that the angle of incidence θw2 represented by the above-described equation (10) becomes about 14°. These angles of incidence θw1 and θw1 satisfy the above-described equation (11).

The straight beam probe 12 incorporated in the ultrasonic probe 1B is arranged so that a transducer surfaces SO thereof passes through the center O of the spheroid and is along a straight line L (corresponding to the rotational axis of the spheroid) meeting orthogonal to the two parallel planes (immediately above the center O of the spheroid in the example shown in FIG. 12). Thus, simultaneously with ultrasonic testing by an angle beam method using the transducers 11A to 11D, an advantage of being able to perform thickness measurement of the steel pipe P and lamination detection using the straight beam probe 12 is gained.

Then, an ultrasonic testing was carried out in a state where the ultrasonic probe 1B is arranged so as to face the steel pipe P so that the longer axis direction of the ultrasonic probe 1B is along the axial direction of the steel pipe, the shorter axis direction of the ultrasonic probe 1B is along the circumferential direction of the steel pipe, and the center O of the spheroid correctly faces the axial center of the steel pipe P and is located in the vicinity of the external surface of the steel pipe P. Water as a coupling medium was filled between the ultrasonic probe 1B and steel pipe P by supplying water into the cabinet 5 through a water tap 51 provided on a side wall of the cabinet 5.

Just as described for the second example, since the propagation velocity of an ultrasonic wave (ultrasonic shear wave) in the steel pipe is 3200 m/sec and the propagation velocity of an ultrasonic wave (ultrasonic longitudinal wave) in water, which is a coupling medium, is 1500 m/sec, the angle of refraction (angle of refraction corresponding to the angle of incidence θw1) θs (called θs1) of an ultrasonic wave transmitted by the transducers 11A and 11B located on the longer axis of the ultrasonic probe 1B becomes about 41° and the angle of refraction (angle of refraction corresponding to the angle of incidence θw2) θs (called θs2) of an ultrasonic wave transmitted by the transducers 11C and 11D located on the shorter axis of the ultrasonic probe 1B becomes about 31°.

As described above, the external refraction angle θr of an ultrasonic wave becomes equal to the angles of refraction θs1 and θs2, and the internal refraction angle θk is represented as a function of the angle of incidence θw, propagation direction γ, and t/D of the steel pipe P. That is, the internal refraction angle θk takes a minimum value and is equal to the angle of refraction θs1 when the propagation direction γ agrees with the axial direction of the steel pipe P. In other words, the internal refraction angle θk related to the transducers 11A and 11B becomes about 41°. The angle of refraction θs generally increases as the propagation direction γ deflects from the axial direction of the steel pipe P to the circumferential direction and the internal refraction angle θk takes a maximum value, which is represented by the above-described equation (8), when the propagation direction γ agrees with the circumferential direction of the steel pipe P. In the present example, the internal refraction angle θk related to the transducers 11C and 11D is obtained by substituting t/D=11% and θs (θs2)=31° into the equation (8), yielding about 41°, which is an equivalent value of the internal refraction angle θk when the propagation direction γ agrees with the axial direction of the steel pipe P.

Since the shape of the ultrasonic probe 1B according to the present example (arrangement condition of the transducers 11A to 11D) is determined as described above, it is possible to cause the propagation direction γ of an ultrasonic wave transmitted by each of the transducers 11A to 11D and the extension direction of flaws to be detected to are orthogonal to each other and, at the same time, to maintain the internal refraction angle θk approximately constant regardless of the tilt angle.

In other words, it is possible to detect flaws extending in the circumferential direction of the steel pipe P by the transducers 11A and 11B arranged along the axial direction of the steel pipe P and flaws extending in the axial direction of the steel pipe P by the transducers 11C and 11D arranged along the circumferential direction of the steel pipe P with high precision respectively.

In the present example, ultrasonic testing is conducted by rotating the steel pipe P in the circumferential direction and moving the steel pipe P in the axial direction. In addition, the ultrasonic testing equipment 100B has, preferably, a follow-up apparatus for maintaining a relative position of the ultrasonic probe 1A with respect to the steel pipe P approximately constant in a plane orthogonal to the axial direction of the steel pipe P. A more concrete description will be given below with reference to FIG. 13 when deemed appropriate.

Figure 13:
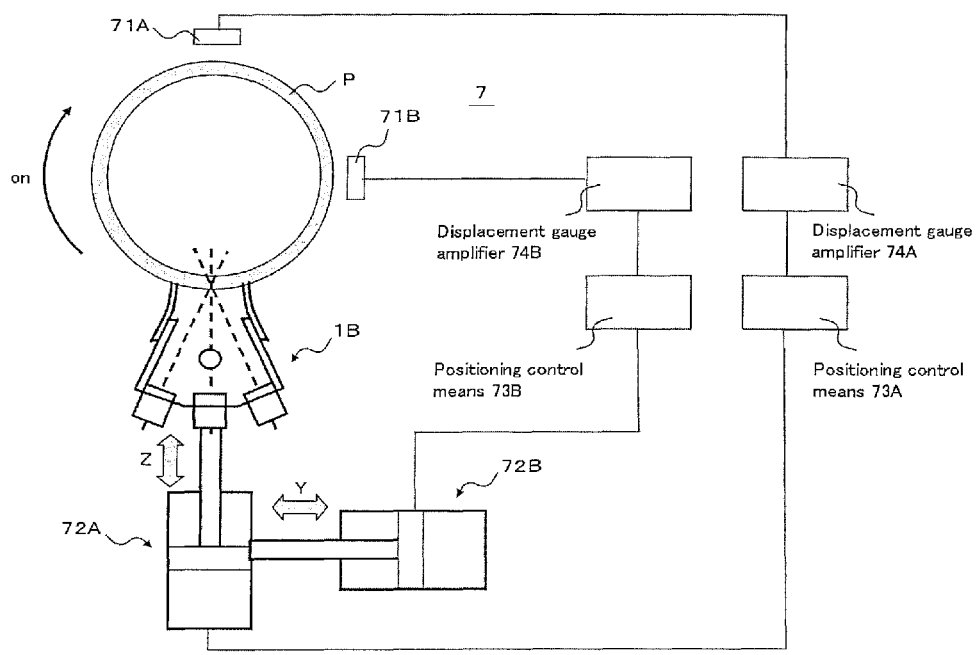
FIG. 13 shows the outline configuration of a follow-up apparatus incorporated in the ultrasonic testing equipment according to the fourth example of the present invention.

FIG. 13 shows the outline configuration of a follow-up apparatus incorporated in the ultrasonic testing equipment 100B according to the present example. A follow-up apparatus 7 in the present example has, as shown in FIG. 13, one or more (two in the present example) non-contact displacement gauges (for example, laser displacement gauges, vortex displacement gauges, ultrasonic displacement gauges and so on) 71A and 71B for measuring the distance up to the external surface of the steel pipe P, positioning mechanisms (hydraulic cylinders in the present example) 72A and 72B for moving the ultrasonic probe 1B along two directions (the vertical direction (Z direction) and the horizontal direction (Y direction) in the present example) orthogonal to the axial direction of the steel pipe P, and positioning control means (hydraulic controllers in the present example) 73A and 73B for controlling the positioning mechanisms 72A and 72B.

In the present example, a configuration is adopted in which the distance measured by the non-contact displacement gauge 71A is input into the positioning control means 73A via a displacement gauge amplifier 74A and the distance measured by the non-contact displacement gauge 71B is input into the positioning control means 73B via a displacement gauge amplifier 74B. Then, the positioning control means 73A controls the positioning mechanism 72A (adjusts the position of the ultrasonic probe 1B in the Z direction) based on a measured value of distance input by the non-contact displacement gauge 71A (displacement gauge amplifier 74A) so that the relative position of the ultrasonic probe 1B with respect to the steel pipe P is approximately constant. Similarly, the positioning control means 73B controls the positioning mechanism 72B (adjusts the position of the ultrasonic probe 1B in the Y direction) based on a measured value of distance input by the non-contact displacement gauge 71B (displacement gauge amplifier 74B) so that the relative position of the ultrasonic probe 1B with respect to the steel pipe P is approximately constant.

More concretely, distance measurement up to the external surface of the steel pipe P by the non-contact displacement gauges 71A and 71B is always made continuously when carrying out an ultrasonic testing. Then, the positioning control means 73A drives the positioning mechanism 72A so that a difference between a measured value of distance input by the non-contact displacement gauge 71A and a predetermined standard distance becomes zero. In other words, the positioning control means 73A drives the positioning mechanism 72A to move the ultrasonic probe 1B by a distance corresponding to the difference in the Z direction. At this point, the positioning control means 73A measures an actual value of drive amount (distance of moving the ultrasonic probe 1B in the Z direction) of the positioning mechanism 72A as occasion requires, and the positioning mechanism 72A is driven until the actually measured value becomes equal to the difference to improve arranging accuracy. Incidentally, the positioning mechanism 72A is driven by the positioning control means 73A with timing when an area of the steel pipe P whose distance has been measured by the non-contact displacement gauge 71A reaches, after passing a predetermined time (calculated based on the outer diameter and rotational speed of the steel pipe P), the position where the ultrasonic probe 1B is arranged (that is, the position after 180° rotation).

Similarly, the positioning control means 73B drives the positioning mechanism 72B so that a difference between a measured value of distance input by the non-contact displacement gauge 71B and a predetermined standard distance becomes zero. In other words, the positioning control means 73B drives the positioning mechanism 72B to move the ultrasonic probe 1B by a distance corresponding to the difference in the Y direction. At this point, the positioning control means 73B measures an actual value of drive amount (distance of moving the ultrasonic probe 1B in the Y direction) of the positioning mechanism 72B as occasion requires, and the positioning mechanism 72B is driven until the actually measured value becomes equal to the difference to improve arranging accuracy. Incidentally, the positioning mechanism 72B is driven by the positioning control means 73B with timing when an area of the steel pipe P whose distance has been measured by the non-contact displacement gauge 71B reaches, after passing a predetermined time (calculated based on the outer diameter and rotational speed of the steel pipe P), a position of 180° rotation.

In the present example, a configuration has been described in which the position in the Z direction of the ultrasonic probe 1B is adjusted based on a distance measured by the non-contact displacement gauge 71A and the position in the Y direction of the ultrasonic probe 1B is adjusted based on a distance measured by the non-contact displacement gauge 71B, but the configuration is not limited to this. For example, another configuration can also be adopted in which the position in the Y direction of the ultrasonic probe 1B is adjusted based on a measured value of distance by the non-contact displacement gauge 71A with timing when an area of the steel pipe P whose distance has been measured by the non-contact displacement gauge 71A reaches a position of 90° rotation and the position in the Z direction of the ultrasonic probe 1B is adjusted based on a measured value of distance by the non-contact displacement gauge 71B with timing when an area of the steel pipe P whose distance has been measured by the non-contact displacement gauge 71B reaches a position of 90° rotation.

Since, as described above, the ultrasonic testing equipment 100B according to the present example has, as a preferable configuration, the relative position of the ultrasonic probe 1B with respect to the steel pipe P can be maintained approximately constant by the follow-up apparatus 7 even if the steel pipe P has a cross sectional shape that is not a complete round or an axial bend has occurred. Therefore, variations in the angle of incidence of an ultrasonic wave into the steel pipe P from each of the transducers 11A to 11D of the ultrasonic probe 1B are suppressed and, as a result, detectability of flaws can be maintained approximately constant.

Here, like the ultrasonic testing equipment according to the first and second examples, in the ultrasonic testing equipment 100B according to the present example, the transmission/reception control means controls transmission time-shift or reception time-shift of an ultrasonic wave of each of the transducers 11A to 11D so that each surface echo on the steel pipe P of an ultrasonic wave transmitted by each of the transducers 11A to 11D is received at approximately the same time. Then, like the ultrasonic testing equipment according to the first and second examples, an echo received by each of the transducers 11A to 11D is synthesized and flaws are detected based on the synthesized echo. Therefore, flaws in four directions can approximately simultaneously detected. This enables quadrupling of ultrasonic testing speed, compared with the conventional time division ultrasonic testing (first: ultrasonic testing using the transducer 11A, second: ultrasonic testing using the transducer 11B, third: ultrasonic testing using the transducer 11C, fourth: ultrasonic testing using the transducer 11D, fifth: ultrasonic testing using the transducer 11A, hereafter repeated).

Figure 14:
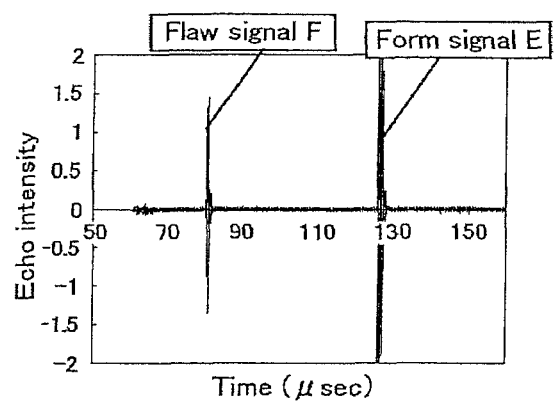
FIG. 14 illustrates ultrasonic testing waveforms obtained when an ultrasonic wave is transmitted and received by only one transducer in the ultrasonic testing equipment according to the fourth example of the present invention.
Figure 15:
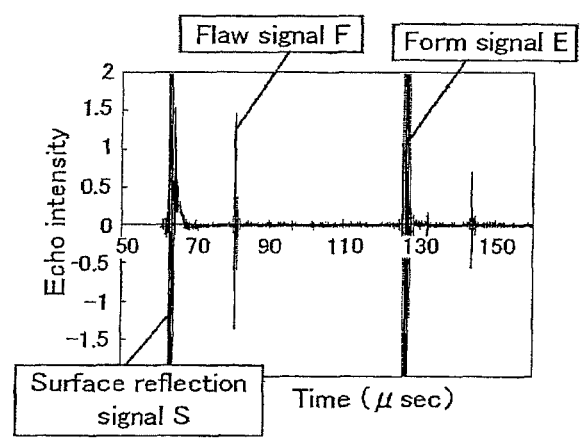
FIG. 15 illustrates ultrasonic testing waveforms obtained when, by controlling transmission time-shift or reception time-shift of each of four transducers so that each surface echo is received at approximately the same time, an ultrasonic wave is transmitted and received by each transducer in the ultrasonic testing equipment according to the fourth example of the present invention.

FIG. 14 illustrates ultrasonic testing waveforms (waveforms of echoes received by the transducer A) obtained when an ultrasonic wave is transmitted and received by the transducer A only in the ultrasonic testing equipment 100B according to the present example. FIG. 15 illustrates ultrasonic testing waveforms (waveforms obtained by synthesizing echoes received by the transducers 11A to 11D) obtained when, by controlling transmission time-shift or reception time-shift of each of the transducers 11A to 11D so that each surface echo is received at approximately the same time, an ultrasonic wave is transmitted and received by each of the transducers 11A to 11D in the ultrasonic testing equipment 100B according to the present example.

An occurrence of a form signal E is characteristic of the ultrasonic testing waveforms shown in FIG. 14 compared with ultrasonic testing waveforms obtained when general ultrasonic testing is carried out. In ultrasonic testing waveforms shown in FIG. 15, an occurrence of a surface reflection signal S, in addition to the form signal E, is characteristic. Occurrences of these form signals E and the surface reflection signal S are due to two transducers arranged so as to face each other. That is, because, the transducers 11A and 11B are arranged symmetric with respect to a straight line L and the transducers 11C and 11D are arranged symmetric with respect to the straight line L.

Figure 16:
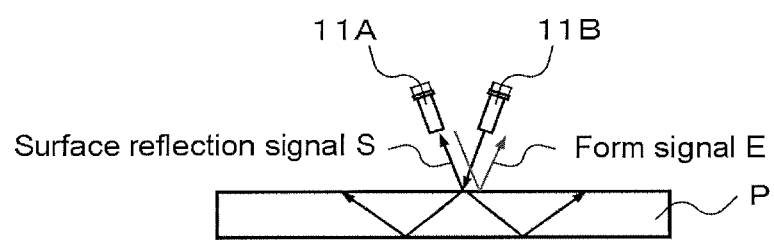
FIG. 16 is an illustration showing propagation behavior of an ultrasonic wave in the ultrasonic testing equipment according to the fourth example of the present invention.

More concretely, as shown in FIG. 16, the form signal E corresponds, for example, to an echo received by the transducer 11B of an ultrasonic wave transmitted by the transducer 11B after being reflected on an external surface of the steel pipe P, then reflected on the transducer 11A arranged so as to face the transducer 11B, and again reflected on the external surface of the steel pipe P. The surface reflection signal S corresponds, for example, to an echo received by the transducer 11A arranged so as to face the transducer 11B of an ultrasonic wave transmitted by the transducer 11B after being reflected on the external surface of the steel pipe P.

As described above, characteristic signals (signals that occur regardless of whether there is a flaw or not) such as the form signal E and surface reflection signal S occur in the ultrasonic testing waveforms obtained by the ultrasonic testing equipment 100B according to the present example. However, by adjusting the distance h from the center O of the spheroid of the ultrasonic probe 1B (See FIG. 5) while maintaining a condition of arranging the ultrasonic probe 1B so that the center O of the spheroid correctly faces the axial center of the steel pipe P and is located in the vicinity of the external surface of the steel pipe P, flaw signals of the internal and external surfaces can be caused to occur between the surface reflection signal S and form signal E, and thus flaws can be detected like conventional ultrasonic testing using the angle beam method.

Here, a reason why transmission time-shift or reception time-shift of an ultrasonic wave transmitted by each of the transducers 11A to 11D is controlled so that each surface echo on the steel pipe P is received at approximately the same time is described below.

That is, (1) a surface reflection signal produced through reception by the transducer 11B of an ultrasonic wave transmitted by the transducer 11A, (2) a surface reflection signal produced through reception by the transducer 11A of an ultrasonic wave transmitted by the transducer 11B, (3) a surface reflection signal produced through reception by the transducer 11D of an ultrasonic wave transmitted by the transducer 11C, and (4) a surface reflection signal produced through reception by the transducer 11C of an ultrasonic wave transmitted by the transducer 11D are caused to occur approximately at the same time.

Also, (5) a form signal produced through reflection on the transducer 11B and reception by the transducer 11A of an ultrasonic wave transmitted by the transducer 11A, (6) a form signal produced through reflection on the transducer 11A and reception by the transducer 11B of an ultrasonic wave transmitted by the transducer 11B, (7) a form signal produced through reflection on the transducer 11D and reception by the transducer 11C of an ultrasonic wave transmitted by the transducer 11C, and (8) a form signal produced through reflection on the transducer 11C and reception by the transducer 11D of an ultrasonic wave transmitted by the transducer 11D are caused to occur approximately at the same time.

Duration (width of waveforms) of the form signal E (signal after synthesizing each form signal of the above (5) to (8)) and the surface reflection signal S (signal after synthesizing each surface reflection signal of the above (1) to (4)) shown in FIG. 15 can be shortened through control as described above, and thus a dead zone resulting from occurrence of these characteristic signals can now be made narrower.

Since the ultrasonic testing equipment 100B according to the present example described above has the ultrasonic probe 1B with a very compact structure, while realizing approximately at the same time ultrasonic testing by the angle beam and normal beam methods in four directions, the follow-up apparatus 7 having a pair of non-contact displacement gauges 71A and 71B, the hydraulic cylinders 72A and 72B, and the hydraulic controllers 73A and 73B could be integrated. Therefore, it became possible to simplify equipment and reduce costs while improving ultrasonic testing efficiency. Also, because the follow-up apparatus 7 was selected to be a non-contact type, it became possible to detect flaws throughout the steel pipe P including pipe ends with high precision while improving tracking at pipe ends of the steel pipe P.

The invention claimed is:

1. An ultrasonic testing equipment for detecting a flaw by ultrasonic waves in a tubular test object, comprising
   an ultrasonic probe including a plurality of transducers arranged along an annular curved surface; and
   a transmission/reception control device that controls transmission/reception of ultrasonic waves by said ultrasonic probe, wherein
   said annular curved surface is obtained by cutting a predetermined spheroid with two parallel planes facing to each other that do not pass through a center of the spheroid and do not sandwich the center of the spheroid, said two parallel planes being orthogonal to a rotational axis of the spheroid,
   a shape of said annular curved surface is determined so that when transducers appropriately selected from said plurality of transducers are caused to transmit and receive ultrasonic waves, respective internal refraction angles $\theta_K$ of the ultrasonic waves are approximately equivalent regardless of propagation directions of the ultrasonic waves,
   said ultrasonic probe is arranged so as to face said tubular test object so that a longer axis direction of said annular curved surface is along a longitudinal axial direction of said tubular test object, a shorter axis direction of said annular curved surface is along a circumferential direction of said tubular test object and the center of said spheroid correctly faces a longitudinal axial center of said tubular test object, and
   said transmission/reception control device causes at least two transducers among said plurality of transducers to transmit the ultrasonic waves to and receive the same from said tubular test object.

2. The ultrasonic testing equipment according to claim 1, wherein said ultrasonic probe further comprises at least one straight beam probe arranged along a straight line that passes through the center of said spheroid and is orthogonal to said two parallel planes.

3. The ultrasonic testing equipment according to claim 1, wherein said ultrasonic probe is arranged so that the center of said spheroid is located in a vicinity of an external surface of said tubular test object.

4. The ultrasonic testing equipment according to claim 1, wherein
   said transmission/reception control device controls transmission time-shift or reception time-shift of the ultrasonic waves of one transducer and another transducer among at least two transducers that transmit the ultrasonic waves to and receive the same from said tubular test object, so that a surface echo on said tubular test object of the ultrasonic wave transmitted from said one transducer and another surface echo on said tubular test object of the ultrasonic wave transmitted from said another transducer are received at approximately the same time.

5. The ultrasonic testing equipment according to claim 1, wherein an adjustment device that adjusts an angle of incidence of the ultrasonic wave transmitted from each of said plurality of transducers to said tubular test object is provided.

6. The ultrasonic testing equipment according to claim 5, wherein
   each of said plurality of transducers has a plurality of piezoelectric elements divided into a rectangular shape along a radial direction of the annular curved surface in each transducer, and
   said adjustment device adjusts the angle of incidence of the ultrasonic wave transmitted to said tubular test object by electrically controlling transmission/reception time-shift of the ultrasonic wave by said plurality of piezoelectric elements.

7. The ultrasonic testing equipment according to claim 1, comprising a follow-up apparatus for maintaining a relative position of said ultrasonic probe with respect to said tubular test object approximately constant in a plane orthogonal to the longitudinal axial direction of said tubular test object.

8. The ultrasonic testing equipment according to claim 7, wherein
   said follow-up apparatus comprises one or more non-contact displacement gauges for measuring a distance up to the external surface of said tubular test object, a positioning mechanism for moving said ultrasonic probe along two directions orthogonal to the longitudinal axial direction of said tubular test object and a positioning control device that controls the positioning mechanism; and
   said positioning control device controls said positioning mechanism based on the distance measured by said non-contact displacement gauges so that the relative position of said ultrasonic probe with respect to said tubular test object is approximately constant.

9. An ultrasonic testing method wherein, using the ultrasonic testing equipment according to claim 1 and comprising the steps of,
   relatively rotating said ultrasonic probe along the circumferential direction of said tubular test object and relatively moving the same along the axial direction of said tubular test object while said transmission/reception control device are controlling transmission/reception of ultrasonic waves by said ultrasonic probe; and
   detecting a flaw in all or part of said tubular test object based on echoes received by said ultrasonic probe.

10. A manufacturing method of a seamless pipe or tube comprising the steps of:
   manufacturing a seamless pipe or tube by piercing a billet, and
   detecting a flaw in the seamless pipe or tube by using the ultrasonic testing method according to claim 9.

* * * * *